(12) United States Patent
Bates et al.

(10) Patent No.: US 10,238,636 B2
(45) Date of Patent: Mar. 26, 2019

(54) METHODS OF TREATING LIVER DISEASE

(71) Applicant: Gilead Sciences, Inc., Foster City, CA (US)

(72) Inventors: Jamie Geier Bates, Burlingame, CA (US); David Gordon Clarkson Breckenridge, San Mateo, CA (US); John T. Liles, San Jose, CA (US); William J. Watkins, Saratoga, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 15/508,968

(22) PCT Filed: Sep. 22, 2015

(86) PCT No.: PCT/US2015/051529
§ 371 (c)(1),
(2) Date: Mar. 6, 2017

(87) PCT Pub. No.: WO2016/049069
PCT Pub. Date: Mar. 31, 2016

(65) Prior Publication Data
US 2017/0273952 A1 Sep. 28, 2017

Related U.S. Application Data

(60) Provisional application No. 62/054,767, filed on Sep. 24, 2014.

(51) Int. Cl.
*A61K 31/42* (2006.01)
*A61K 45/06* (2006.01)
*A61K 9/48* (2006.01)
*A61K 31/4439* (2006.01)

(52) U.S. Cl.
CPC ............. *A61K 31/42* (2013.01); *A61K 9/48* (2013.01); *A61K 31/4439* (2013.01); *A61K 45/06* (2013.01); *A61K 2300/00* (2013.01)

(58) Field of Classification Search
CPC ...... A61K 31/42; A61K 9/48; A61K 31/4439; A61K 45/06; A61K 2300/00
USPC ........................................................ 514/893
See application file for complete search history.

(56) References Cited

U.S. PATENT DOCUMENTS

| | | |
|---|---|---|
| 8,263,595 B2 | 9/2012 | Swinnen et al. |
| 8,378,108 B2 | 2/2013 | Corkey et al. |
| 8,552,196 B2 | 10/2013 | Corkey et al. |
| 8,598,360 B2 | 12/2013 | Corkey et al. |
| 8,742,126 B2 | 6/2014 | Notte et al. |
| 9,067,933 B2 | 6/2015 | Corkey et al. |
| 9,254,284 B2 | 2/2016 | Notte et al. |
| 9,333,197 B2 | 5/2016 | Notte et al. |
| 9,586,932 B2 | 3/2017 | Corkey et al. |
| 9,750,730 B2 | 9/2017 | Notte et al. |
| 9,873,682 B2 | 1/2018 | Notte et al. |
| 2003/0203939 A1 | 10/2003 | Kliewer et al. |
| 2006/0223996 A1 | 10/2006 | Sun et al. |
| 2007/0167386 A1 | 7/2007 | Otsu et al. |
| 2007/0237770 A1 | 10/2007 | Lai et al. |
| 2007/0276050 A1 | 11/2007 | Koch et al. |
| 2009/0318425 A1 | 12/2009 | Chang et al. |
| 2009/0318435 A1 | 12/2009 | Hays et al. |
| 2010/0029619 A1 | 2/2010 | Uchikawa et al. |
| 2010/0184809 A1 | 7/2010 | Kremoser et al. |
| 2010/0210660 A1 | 8/2010 | Kremoser et al. |
| 2011/0009410 A1 | 1/2011 | Corkey et al. |
| 2011/0077235 A1 | 3/2011 | Chang et al. |
| 2012/0004267 A1 | 1/2012 | Corkey et al. |
| 2012/0232116 A1 | 9/2012 | Kremoser et al. |
| 2012/0316194 A1 | 12/2012 | Chang |
| 2013/0197037 A1* | 8/2013 | Notte .................. C07D 213/56 514/341 |
| 2014/0018370 A1 | 1/2014 | Corkey et al. |
| 2014/0038957 A1 | 2/2014 | Witty et al. |
| 2014/0039007 A1 | 2/2014 | Tully et al. |
| 2014/0057886 A1 | 2/2014 | Pellicciari et al. |
| 2014/0134262 A1 | 5/2014 | Arai et al. |
| 2014/0179663 A1 | 6/2014 | Notte |
| 2014/0187633 A1 | 7/2014 | Manku et al. |
| 2014/0221659 A1 | 8/2014 | Kinzel et al. |
| 2017/0196844 A1 | 7/2017 | Graupe |
| 2018/0099950 A1 | 4/2018 | Notte et al. |

FOREIGN PATENT DOCUMENTS

| | | |
|---|---|---|
| EP | 1677113 | 7/2006 |
| EP | 2058309 | 5/2009 |
| WO | WO-1998034946 | 8/1998 |
| WO | WO-2000056866 | 9/2000 |
| WO | WO-2001068850 | 9/2001 |

(Continued)

OTHER PUBLICATIONS

Adorini, et al., (2012), "Farnesoid X receptor targeting to treat nonalcoholic steatohepatitis", Drug Discov Today, 17:988-97.
Budas, et al., (2016), "Combination of an ASK1 Inhibitor and FXR Agonist Increases Antifibrotic Efficacy in a Rat Model of NASH", Presented at AASLD: The Liver Meeting (R), 1 pg.
Hayakawa, et al., (2012), "Therapeutic targets in the ASK1-dependent stress signaling pathways", Proc Jpn Acad Ser B Phys Biol Sci., 88:434-53.
IPRP for PCT/US2015/051529, dated Mar. 28, 2017, 28pp.
ISR & Written Opinion for PCT/US2015/051529, dated Mar. 3, 2016, 21pp.
Neuschwander-Tetri, et al., (2012), "Farnesoid x receptor agonists: what they are and how they might be used in treating liver disease", Curr Gastroenterol Rep., 14:55-62.

(Continued)

*Primary Examiner* — Kristin A Vajda
(74) *Attorney, Agent, or Firm* — Sheppard Mullin Richter & Hampton LLP

(57) ABSTRACT

The present disclosure relates to a method of preventing and/or treating liver disease comprising administering an ASK1 inhibitor in combination with a FXR agonist, to a patient in need thereof.

18 Claims, No Drawings

(56) References Cited

FOREIGN PATENT DOCUMENTS

| | | | |
|---|---|---|---|
| WO | WO-2005/032549 A1 | 4/2005 | |
| WO | WO 2005032549 A1 * | 4/2005 | ............ A61K 31/42 |
| WO | WO-2006036941 | 4/2006 | |
| WO | WO-2008016131 | 2/2008 | |
| WO | WO-2008042867 | 4/2008 | |
| WO | WO-2008073919 | 6/2008 | |
| WO | WO-2009011850 | 1/2009 | |
| WO | WO-2009027283 | 3/2009 | |
| WO | WO-2009123986 | 10/2009 | |
| WO | WO-2010045470 | 4/2010 | |
| WO | WO-2010056982 | 5/2010 | |
| WO | WO-2010111464 | 9/2010 | |
| WO | WO-2011008709 | 1/2011 | |
| WO | WO-2011/041293 A1 | 4/2011 | |
| WO | WO-2011097079 | 8/2011 | |
| WO | WO-2011097594 | 8/2011 | |
| WO | WO-2011119894 | 9/2011 | |
| WO | WO-2012068464 | 5/2012 | |
| WO | WO-2012080735 | 6/2012 | |
| WO | WO-2012115885 | 8/2012 | |
| WO | WO-2012170711 | 12/2012 | |
| WO | WO-2013006485 | 1/2013 | |
| WO | WO-2013/112741 A1 | 8/2013 | |

OTHER PUBLICATIONS

Norman, (2012), "Evaluation of WO2012003387, Gilead's ASK1 inhibitors", Expert Opin Ther Pat., 22:455-9.

Schwabl, et al., (2015), "G18 : The FXR agonist PX20606 reduces liver damage, fibrosis and portal hypertension in cirrhotic rats", Journal of Hepatology, The Home of Liver Research, 62:S238.

Yoshida, et al., (2012), "Pharmacologic inhibition of ASK1 attenuates hepatocyte apoptosis and limits hepatotoxin-induced liverfibrosis progression in mice", Hepatology, 56:771A-772A.

Zhang, et al., (2009), "Farnesoid X receptor agonist WAY-362450 attenuates liver inflammation and fibrosis in murine model of non-alcoholic steatohepatitis", Journal of Hepatology, Elsevier, Amsterdam, NL, 51:380-88.

Bataller et al., Liver Fibrosis, the Journal of Clinical Investigation, vol. 115, No. 2, 2005, pp. 209-218.

Chen et al., Curcumin inhibits thrombin-stimulated connective tissue growth factor (CTGF/CCN2) production through c-Jun NH2-terminal kinase suppression in human gingival fibroblasts, Journal of Periodontology (20121231), 83(12), pp. 1546-1553 in English, Coden: JOPRAJ ISSN: 0022-3492.

Ebrahimian et al., Cardiac hypertrophy is associated with altered thioredoxin and ASK-1 signaling in a mouse model of menopause, American Journal of Physiology (20081031), 295(4), pp. h1481-h1488 in English, Additional Information: Pt. 2, Coden: AJPHAP ISSN: 0002-9513.

Fan et al., Small Heat-Shock Protein Hsp20 Attenuates β-Agonist-Mediated Cardiac Remodeling Through Apoptosis Signal-Regulating Kinase 1, Circulation Research (20061124), 99(11), pp. 1233-1242 in English, Coden: CIRUAL ISSN: 0009-7330.

Gan et al., Role of FIP200 in cardiac and liver development and its regulation of TNFα and Tsc-mTOR signaling pathways, Journal of Cell Biology (20061009), 175(1), pp. 121-133 in English, Coden: JCLBA3 ISSN: 0021-9525.

Gilot et al., ASK(1) and you shall receive: a new link between antioxidants and cell death signalling, Hepatology (Philadelphia, Pa, United States) (20030731), 38(1), pp. 252-254 in English, Coden: HPTLD9 ISSN: 0270-9139.

Gilot et al., Liver protection from apoptosis requires both blockage of initiator caspase activities and inhibition of ASK1/JNK pathway via glutathione S-transferase regulation, Journal of Biological Chemistry (20021220), 277(51), pp. 49220-49229 in English, Coden: JBCHA3 ISSN: 0021-9258.

Guo et al., Differential expression of the Toll-like receptor pathway and related genes of chicken bursa after experimental infection with infectious bursa disease virus, Archives of Virology (2012), 157(11), pp. 2189-2199 in English, Coden: ARVIDF ISSN: 0304-8608.

Guo et al. (2010) "Regulation of the Severity of Neuroinflammation and demyelination by TLR-ASL1-p38 Pathway" EMBO Molecular Medicine (1):1-12.

Guo et al. (2010) "Regulation of the Severity of Neuroinflammation and demyelination by TLR-ASL1-p38 Pathway" Supporting Information: 1-25.

Guo, (2003) "The Relationships Between the Medicines' Chemical Structures and the Bioactivities Thereof," China Medical Science Press, 2nd Ed. pp. 131-132.

Hattori et al. (2009) "The roles of ASK family proteins in stress responses and diseases", Cell Comunication and Signaling, 7:9 pp. 1-10.

Hikoso et al., Progression of Heart Failure Was Suppressed by Inhibition of Apoptosis Signal-Regulating Kinase 1 Via Transcoronary Gene Transfer, Journal of the American College of Cardiology (20070731), 50(5), pp. 453-462 in English, Coden: Jaccdi ISSN: 0735-1097.

Hori et al., Oxidative stress and left ventricular remodelling after myocardial infarction, Cardiovascular Research (20090215), 81(3), pp. 457-464 in English, Coden: Cvreau ISSN: 0008-6363.

Hu et al., Class A scavenger receptor attenuates myocardial infarction-induced cardiomyocyte necrosis through suppressing M1 macrophage subset polarization, Basic Research in Cardiology (20111130), 106(6), pp. 1311-1328 in English, Coden: BRCAB7 ISSN: 0300-8428.

Ichijo et al. (1997) "Induction of Apoptosis by ASK1, a Mammalian MAPKKK that Activates SAPK/JNK and p38 Signaling Pathways", Science, vol. 275, pp. 90-94.

Iriyama et al. (2009), "ASK1 and ASK2 differently regulate the counteracting roles of apoptosis and inflammation in tumorigensis", the European Molecular Biology Organization Journal, pp. 1-11.

Izumiya et al., Apoptosis Signal-Regulating Kinase 1 Plays a Pivotal Role in Angiotensin II-Induced Cardiac Hypertrophy and Remodeling, Circulation Research (20031031), 93(9), pp. 874-883 in English, Coden: Cirual ISSN: 0009-7330.

Kataoka et al., Apoptosis signal-regulating kinase 1 deficiency eliminates cardiovascular injuries induced by high-salt diet, Journal of Hypertension (2010), vol. Date: 2011, 29(1), pp. 76-84 in English, Coden: JOHYD3 ISSN: 0263-6352.

Kim et al., Inhibition of liver X receptor-α-dependent hepatic steatosis by isoliquiritigenin, a licorice antioxidant flavonoid, as mediated by JNK1 inhibition, Free Radical Biology & Medicine (20101201), 49(11), pp. 1722-1734 in English, Coden: FRBMEH ISSn: 0891-5849.

Knittel et al. Drug Design and Relationship of Functional Groups to Pharmacological Activity; Foye's Principles of Medicinal Chemistry, 5th Edition, Lippincott Williams & Wilkins; ed. David A. Williams and Thomas L. Lemke; 2002; 37-67.

Kudo et al., Lipopolysaccharide triggered TNF-α-induced hepatocyte apoptosis in a murine non-alcoholic steatohepatitis model, Journal of Hepatology (20090731), 51(1), pp. 168-175 in English, Coden: Joheec ISSN: 0168-8278.

Kumar et al. (2003) "P38 Map Kinases: Key Singalling Molecules as Therapeutic Targets for Inflammatory Diseases", Nature Reviews, vol. 2, pp. 717-726.

Lim et al., Cannabidiol causes activated hepatic stellate cell death through a mechanism of endoplasmic reticulum stress-induced apoptosis, Cell Death & Disease (20110630), 2(Jun.), pp. e170/1-e170/11, 11 in English, Coden: CDDEA4 ISSN: 2041-4889, URL: http://www.nature.com/cddis/journal/v2/n6/pdf/cddis201152a.pdf.

Manapov et al., Translocation of p21Cip1/WAF1 from the nucleus to the cytoplasm correlates with pancreatic myofibroblast to fibroblast cell conversion, Gut (20050630), 54(6), pp. 814-822 in English, Coden: Guttak ISSN: 0017-5749.

Matkovich et al., Direct and Indirect Involvement of MicroRNA-499 in Clinical and Experimental Cardiomyopathy, Circulation Research (2012), 111(5), pp. 521-531 in English, Coden: CIRUAL. ISSN: 0009-7330.

(56) References Cited

OTHER PUBLICATIONS

Mnich et al (2010) "Critical Role for Apoptosis Signal-regulating Kinase 1 in the Development of Inflammatory K/BxN Serum-induced Arthritis" *International Immunopharmacology*(10): 1170-1176.
Nagai et al. (2007) "Pathophysiological Roles of Ask-1 Map Kinase Signaling Pathways", Journal of Biochemistry and Molecular Biology, vol. 40, pp. 1-6.
Nakamura et al., Critical Role of Apoptosis Signal-Regulating Kinase 13 in Aldosterone/Salt-Induced Cardiac Inflammation and Fibrosis, Hypertension (20090930), 54(3), pp. 544-551 in English, Coden: HPRTDN Issn: 0194-911X.
Nako et al., Novel mechanism of angiotensin II-induced cardiac injury in hypertensive rats: the critical role of ASK1 and VEGF, Hypertension Research (2012), 35(2), pp. 194-200 in English, Coden: HRESE4 ISSN: 0916-9636.
Okamoto et al (2010) "Identification of Novel ASK1 Inhibitors Using Virtual Screening" *Bioorganic & Medicinal Chemistry*, 1-4.
Okiyama et al., Polyenephosphatidylcholine prevents alcoholic liver disease in PPARα-null mice through attenuation of increases in oxidative stress, Journal of Hepatology (20090630), 50(6), pp. 1236-1246 in English, Coden: JOHEEC ISSN: 0168-8278.
Oshida et al., Toxicological effect of emodin in mouse testicular gene expression profile, Journal of Applied Toxicology (2011), 31(8), pp. 790-800 in English, Coden: JJATDK ISSN: 0260-437X.
Patani et al., Bioisosterism: A Rational Approach in Drug Design. Chem. REv. 1996, 96, 3147-3146.
Pimienta et al. (2007) "Canonical and Alternative MAPK Signaling", Cell Cycle, vol. 6(21), pp. 2628-2632.
Roy et al., Fra-2 mediates oxygen-sensitive induction of transforming growth factor βin cardiac fibroblasts, Cardiovascular Research (20100901), 87(4), pp. 647-655 in English, Coden: CVREAU ISSN: 0008-6363.
Rui et al., JNK-dependent AP-1 activation is required for aristolochic acid-induced TGF-β1 synthesis in human renal proximal epithelial cells, American Journal of Physiology (20120630), 302(6), pp. f1569-f1575 in English Additional Information: Pt. 2, Coden: AJPHAP ISSN: 0002-9513.
Saitoh et al. (1998), "Mammalian thioredoxin is a direct inhibitor of apoptosis signal-regulating kinase (ASK) 1", The European Molecular Biology Organization Journal, vol. 17(9), pp. 2596-2606.
Sedeek et al., Critical role of Nox4-based NADPH oxidase in glucose-induced oxidative stress in the kidney: implications in type 2 diabetic nephropathy, American Journal of Physiology (20101231), 299(6), pp. f1348-f1358 in English, Additional Information: Pt. 2, CODEN: AJPHAP ISSN: 0002-9513.
Sharma et al., Cdc42 and Rac1 are major contributors to the saturated fatty acid-stimulated JNK pathway in hepatocytes, Journal of Hepatology (20120131), 56(1), pp. 192-198 in English, Coden: JOHEEC ISSN: 0168-8278.
Takeda, (2008) "Apoptosis Signal-Regulating Kinase 1 in Stress and Immune Response", Annu. Rev. Pharmacol. Toxicol., 48:8.1-8.27.
Takeda et al. (2007), "Apoptosis Signal-regulating Kinase (ASK) 2 Functions as a Mitogen-activated Protein Kinase Kinase Kinase in a Heteromeric Complex with ASK1", Journal of Biological Chemistry, vol. 282(10), pp. 7522-7531.
Taki et al., Apoptosis signal-regulating kinase 1 is crucial for oxidative stress-induced but not for osmotic stress-induced hepatocyte cell death, Life Sciences (20081219), 83(25-26), pp. 859-864 in English, Coden: LIFSAK ISSN: 0024-3205.
Taniike et al., Apoptosis Signal-Regulating Kinase 1/p38 Signaling Pathway Negatively Regulates Physiological Hypertrophy, Circulation (20080129), 117(4), pp. 545-552 in English, Coden: Circaz ISSN: 0009-7322.
Terada et al., (2007), Important role of of apoptosis signal-regulating kinase 1 in ischemic acute kidney injury, BBRC, 354:1043-1049.
Thandavarayan et al., 14-3-3 protein regulates Ask1 signaling and protects against diabetic cardiomyopathy, Biochemical Pharmacology (20080501), 75(9), pp. 1797-1806 in English, Coden: BCPCA6 ISSN: 0006-2952.
Toldo et al., Inhibition of apoptosis signal-regulating kinase 1 reduces myocardial ischemia—reperfusion injury in the mouse, Journal of the American Heart Association (20121031), 1(5), pp. 002360/1-002360/8 in English, Coden: JAHABZ ISSN: 2047-9980.
Tsujimoto et al., the Antioxidant Edaravone Attenuates Pressure Overload-Induced Left Ventricular Hypertrophy, Hypertension (20050531), 45(5), pp. 921-926 in English, Coden: HPRTDN ISSN: 0194-911X.
Volynets et al. (2010) "Identification of 3$H$-Naphtho[1,2,3-*de*]quinoline-2,7-diones as Inhibitors of Apoptosis Signal-Regulating Kinase 1 (ASK1)" *Journal of Medicinal Chemistry*:1-7.
Wang et al. (1998), "MAPKKK6, a Novel Mitogen-Activiated Protein Kinase Kinase Kinase, That Associates with MAPKKK5", Biochemical and Biophysical Research Communications, vol. 253, pp. 33-37.
Xue et al., Elevated myocardial Na+/H+ exchanger isoform 1 activity elicits gene expression that leads to cardiac hypertrophy, Physiological Genomics (20100831), 42(3), pp. 374-383 in English, Coden: PHGEFP ISSN: 1094-8341, URL: http://physiolgenomics.physiology.org/cgi/reprint/42/3/374.
Yamaguchi et al., Cardiac-specific disruption of the c-raf-1 gene induces cardiac dysfunction and apoptosis, Journal of Clinical Investigation (20041031), 114(7), pp. 937-943 in English, Coden: JCINAO ISSN: 0021-9738.
Yamamoto et al., Olmesartan Prevents Cardiovascular Injury and Hepatic Steatosis in Obesity and Diabetes, Accompanied by Apoptosis Signal Regulating Kinase-1 Inhibition, Hypertension (20080930), 52(3), pp. 573-580 in English, Coden: HPRTDN ISSN: 0194-911X.
Yamashita et al., Apoptosis signal-regulating kinase-1 is involved in vascular endothelial and cardiac remodeling caused by nitric oxide deficiency, Hypertension (20070930), 50(3), pp. 519-524 in English, Coden: HPRTDN ISSN: 0194-911X.
Yang et al., TLR4 activity is required in the resolution of pulmonary inflammation and fibrosis after acute and chronic lung injury, American Journal of Pathology (20120131), 180(1), pp. 275-292 in English, Coden: AJPAA4 ISSN: 0002-9440.
Ye et al., Dermatophagoides pteronyssinus 2 regulates nerve growth factor release to induce airway inflammation via a reactive oxygen species-dependent pathway, American Journal of Physiology (20110228), 300(2), pp. I216-I224 in English, Additional Information: Pt. 1,Coden: AJPHAP ISSN:0002-9513.
Zhang et al., Tumor necrosis factorα accelerates apoptosis of steatitic hepatocytes from a murine model of non-alcoholic fatty liver disease, Biochemical and Biophysical Research Communications (20100122), 391(4), pp. 1731-1736 in English, Coden: BBRCA9 ISSN: 0006-291X.
Zhang et al. (1999), "Suppression of apoptosis signal-regulating kinase 1-induced cell death by 14-3-3 proteins", Proc. Natl. Acad. Sci, vol. 96, pp. 8511-8515.
Zuo et al., Oligomerized grape seed proanthocyanidins ameliorates isoproterenol-induced cardiac remodeling in rats: role of oxidative stress, Phytotherapy Research (20110531), 25(5), pp. 732-739 in English, Coden: PHYREH ISSN: 0951-418X.

\* cited by examiner

METHODS OF TREATING LIVER DISEASE

CROSS-REFERENCE TO RELATED APPLICATIONS

This application is a national stage entry of International Application No. PCT/US2015/051529, filed Sep. 22, 2015, which claims the benefit of U.S. Application Ser. No. 62/054,767, filed Sep. 24, 2014, the entireties of which are incorporated herein by reference.

FIELD

The present disclosure relates to a method of preventing and/or treating liver disease.

BACKGROUND

Liver disease is generally classified as acute or chronic based upon the duration of the disease. Liver disease may be caused by infection, injury, exposure to drugs or toxic compounds, alcohol, impurities in foods, and the abnormal build-up of normal substances in the blood, an autoimmune process, a genetic defect (such as haemochromatosis), or unknown cause(s).

Liver disease is a leading cause of death world wide. In particular, it has been seen that a diet high in fat damages the liver in ways that are surprisingly similar to hepatitis. The American Liver Foundation estimates that more than 20 percent of the population has non-alcoholic fatty liver disease (NAFLD). It is suggested that obesity, unhealthy diets, and sedentary lifestyles may contribute to the high prevalence of NAFLD. When left untreated, NAFLD can progress to non-alcoholic steatohepatitis (NASH) causing serious adverse effects. Once NASH is developed, it would cause the liver to swell and scar (i.e. cirrhosis) over time.

Although preliminary reports suggest positive lifestyle changes could prevent or reverse liver damage, there are no effective medical treatments for NAFLD. Accordingly, there remains a need to provide new effective pharmaceutical agents to treat liver diseases.

SUMMARY

Disclosed herein is a method of treating and/or preventing liver disease in a patient in need thereof, comprising administering to the patient a therapeutically effective amount of an apoptosis signal regulating kinase 1 (ASK1) inhibitor in combination with a therapeutically effective amount of farnesoid X receptor (FXR) agonist. The liver disease can be any liver disease, including, but not limited to, chronic and/or metabolic liver diseases, nonalcoholic fatty liver disease (NAFLD), and nonalcoholic steatohepatitis (NASH).

In certain embodiments, provided herein is a method of treating and/or preventing nonalcoholic steatohepatitis (NASH) in a patient in need thereof, comprising administering to the patient a therapeutically effective amount of an ASK1 inhibitor in combination with a therapeutically effective amount of a FXR agonist.

In the methods provided herein, the ASK1 inhibitor and the FXR agonist can be coadministered. In such embodiments, the ASK1 inhibitor and the FXR agonist can be administered together as a single pharmaceutical composition, or separately in more than one pharmaceutical composition. Accordingly, also provided herein is a pharmaceutical composition comprising a therapeutically effective amount of an ASK1 inhibitor and a therapeutically effective amount of a FXR agonist.

DETAILED DESCRIPTION

Definitions and General Parameters

As used in the present specification, the following terms and phrases are generally intended to have the meanings as set forth below, except to the extent that the context in which they are used indicates otherwise.

As used herein, the term "about" used in the context of quantitative measurements means the indicated amount ±10%, or alternatively the indicated amount ±5% or ±1%.

As referred to herein, an "ASK1 inhibitor" may be any agent that is capable of inactivating an apoptosis signal regulating kinase 1 (ASK1) protein. The agent may be a chemical compound or biological molecule (e.g., a protein or antibody). The ASK1 protein activity may be measured by several different methods. For example, the activity of an ASK1 protein may be determined based on the ability of the ASK1 protein to phosphorylate a substrate protein. Methods for identifying an ASK1 inhibitor are known (see, e.g., U.S. 2007/0276050 and U.S. 2011/0009410, both of which are incorporated herein by reference in their entirety). Exemplary ASK1 substrate proteins include MAPKK3, MAPKK4, MAPKK6, MAPKK7, or fragments thereof. The ASK1 protein activity may also be measured by the phosphorylation level of the ASK1 protein, for example, the phosphorylation level of a threonine residue in the ASK1 protein corresponding to threonine 838 (T838) of a human full-length ASK1 protein or threonine 845 (T845) of a mouse full-length ASK1 protein. For example, where the ASK1 protein comprises a full-length human ASK1 protein sequence, an ASK1 inhibitor may attenuate phosphorylation of T838 in the full-length human ASK1 protein sequence. A site specific antibody against human ASK1 T838 or mouse ASK1 T845 may be used to detect the phosphohorylation level.

As used herein, a "FXR agonist" refers to any agent that is capable of binding and activating farnesoid X receptor (FXR) which may be referred to as bile acid receptor (BAR) or NR1H4 (nuclear receptor subfamily 1, group H, member 4) receptor. FXR agonist may act as agonists or partial agonists of FXR. The agent may be a chemical compound or biological molecule (e.g., a protein or antibody). The activity of a FXR agonist may be measured by several different methods, e.g. in an in vitro assay using the fluorescence resonance energy transfer (FRET) cell free assay as described in Pellicciari, et al. *Journal of Medicinal Chemistry*, 2002 vol. 15, No. 45:3569-72.

The term "pharmaceutically acceptable salt" refers to salts of pharmaceutical compounds e.g. compound of formula (I) that retain the biological effectiveness and properties of the underlying compound, and which are not biologically or otherwise undesirable. There are acid addition salts and base addition salts. Pharmaceutically acceptable acid addition salts may be prepared from inorganic and organic acids.

Acids and bases useful for reaction with an underlying compound to form pharmaceutically acceptable salts (acid addition or base addition salts respectively) are known to one of skill in the art. Similarly, methods of preparing pharmaceutically acceptable salts from an underlying compound (upon disclosure) are known to one of skill in the art and are disclosed in for example, Berge, at al. *Journal of Pharmaceutical Science*, January 1977 vol. 66, No. 1, and other sources.

As used herein, "pharmaceutically acceptable carrier" includes excipients or agents such as solvents, diluents, dispersion media, coatings, antibacterial and antifungal agents, isotonic and absorption delaying agents and the like that are not deleterious to the disclosed compound or use thereof. The use of such carriers and agents to prepare compositions of pharmaceutically active substances is well known in the art (see, e.g., Remington's *Pharmaceutical Sciences*, Mace Publishing Co., Philadelphia, Pa. 17th Ed. (1985); and *Modern Pharmaceutics*, Marcel Dekker, Inc. 3rd Ed. (G. S. Banker & C. T. Rhodes, Eds.).

The terms "therapeutically effective amount" and "effective amount" are used interchangeably and refer to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease, or the manner of administration as determined by a qualified prescriber or care giver.

The term "treatment" or "treating" means administering a compound or pharmaceutically acceptable salt of formula (I) for the purpose of: (i) delaying the onset of a disease, that is, causing the clinical symptoms of the disease not to develop or delaying the development thereof; (ii) inhibiting the disease, that is, arresting the development of clinical symptoms; and/or (iii) relieving the disease, that is, causing the regression of clinical symptoms or the severity thereof.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and NR$^a$, where R$^a$ is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, $CF_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "lower alkyl" refers to a monoradical branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (in some embodiments, 1, 2 or 3 substituents), as defined for substituted alkyl or a lower alkyl group as defined above that is interrupted by 1, 2, 3, 4 or 5 atoms as defined for substituted alkyl or a lower alkyl group as defined above that has both 1, 2, 3, 4 or 5 substituents as defined above and is also interrupted by 1, 2, 3, 4 or 5 atoms as defined above.

The term "alkylene" refers to a diradical of a branched or unbranched saturated hydrocarbon chain, in some embodiments, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, in some embodiments, having 1, 2, 3, 4, 5 or 6 carbon atoms.

The term "substituted alkylene" refers to an alkylene group as defined above having 1 to 5 substituents (in some embodiments, 1, 2 or 3 substituents) as defined for substituted alkyl.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH═CH$_2$), 1-propylene (or allyl, i.e. —CH$_2$CH═CH$_2$), isopropylene (—C(CH$_3$)═CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkenylene" refers to a diradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "alkynylene" refers to a diradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds.

The term "hydroxy" or "hydroxyl" refers to a group —OH.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl. This term is exemplified by groups such as methoxy, ethoxy, n-propoxy, iso-propoxy, n-butoxy, iso-butoxy, t-butoxy, n-hexyloxy, and the like.

The term "substituted alkoxy" refers to the group R—O—, where R is substituted alkyl or —Y—Z, in which Y is substituted alkylene and Z is substituted alkenyl or substituted alkynyl, where substituted alkyl, substituted alkenyl and substituted alkynyl are as defined herein.

The term "C$_{1-3}$haloalkyl" refers to an alkyl group having from 1 to 3 carbon atoms covalently bonded to from 1 to 7, or from 1 to 6, or from 1 to 3, halogen(s), where alkyl and halogen are defined herein. In some embodiments, C$_{1-3}$haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl.

The term "C$_{1-3}$ hydroxyalkyl" refers to an alkyl group having a carbon atom covalently bonded to a hydroxy, where alkyl and hydroxy are defined herein. In some embodiments, C$_{1-3}$ hydroxyalkyl includes, by way of example, 2-hydroxyethyl.

The term "C$_{1-3}$ cyanoalkyl" refers to an alkyl group having a carbon atom covalently bonded to a cyano, where alkyl and cyano are defined herein. In some embodiments, C$_{1-3}$ cyanoalkyl includes, by way of example, 2-cyanoethyl.

The term "cycloalkyl" refers to cyclic alkyl groups of from 3 to 20 carbon atoms, or from 3 to 10 carbon atoms, having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. The term "substituted cycloalkyl" also includes cycloalkyl groups wherein one or more of the annular carbon atoms of the cycloalkyl group has an oxo group bonded thereto. In addition, a substituent on the cycloalkyl or cycloalkenyl may be attached to the same carbon atom as, or is geminal to, the attachment of the substituted cycloalkyl or cycloalkenyl to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "cycloalkoxy" refers to the group cycloalkyl-O—.

The term "substituted cycloalkoxy" refers to the group substituted cycloalkyl-O—.

The term "cycloalkenyloxy" refers to the group cycloalkenyl-O—.

The term "substituted cycloalkenyloxy" refers to the group substituted cycloalkenyl-O—.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. In addition, a substituent on the heterocyclic group may be attached to the same carbon atom as, or is geminal to, the attachment of the substituted heterocyclic group to the 6,7-ring system. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Examples of heterocyclics include tetrahydrofuranyl, morpholino, piperidinyl, and the like.

The term "heterocycloxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)$_2$-alkyl, —S(O)$_2$-cycloalkyl, —S(O)$_2$-heterocyclyl, —S(O)$_2$-aryl and —S(O)$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, cyano or —S(O)$_n$R$^a$, in which R$^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, or heterocyclyl, or where both R groups are joined to form a heterocyclic group (e.g., morpholino). Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "alkoxycarbonylamino" refers to the group —N(R$^d$)C(O)OR in which R is alkyl and R$^d$ is hydrogen or alkyl. Unless otherwise constrained by the definition, each alkyl may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "aminocarbonylamino" refers to the group —NR$^c$C(O)NRR, wherein R$^c$ is hydrogen or alkyl and each R is hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently hydrogen, alkyl, cycloalkyl, aryl, heteroaryl or heterocyclyl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Liver Diseases

Liver diseases are acute or chronic damages to the liver based in the duration of the disease. The liver damage may be caused by infection, injury, exposure to drugs or toxic compounds such as alcohol or impurities in foods, an abnormal build-up of normal substances in the blood, an autoimmune process, a genetic defect (such as haemochromatosis), or other unknown causes. Exemplary liver diseases include, but are not limited to, cirrhosis, liver fibrosis, non-alcoholic fatty liver disease (NAFLD), non-alcoholic steatohepatitis (NASH), alcoholic steatohepatitis (ASH), hepatic ischemia reperfusion injury, primary biliary cirrhosis (PBC), and hepatitis, including both viral and alcoholic hepatitis.

Non-alcoholic fatty liver disease (NAFLD) is the build up of extra fat in liver cells that is not caused by alcohol. NAFLD may cause the liver to swell (i.e. steatohepatitis), which in turn may cause scarring (i.e. cirrhosis) over time and may lead to liver cancer or liver failure. NAFLD is characterized by the accumulation of fat in hepatocyes and is often associated with some aspects of metabolic syndrome (e.g. type 2 diabetes mellitus, insulin resistance, hyperlipidemia, hypertension). The frequency of this disease has become increasingly common due to consumption of carbohydrate-rich and high fat diets. A subset (~20%) of NAFLD patients develop nonalcoholic steatohepatitis (NASH).

NASH, a subtype of fatty liver disease, is the more severe form of NAFLD. It is characterized by macrovesicular steatosis, balloon degeneration of hepatocytes, and/or inflammation ultimately leading to hepatic scarring (i.e. fibrosis). Patients diagnosed with NASH progress to advanced stage liver fibrosis and eventually cirrhosis. The current treatment for cirrhotic NASH patients with end-stage disease is liver transplant.

A study has shown that a significant proportion of diagnosed NASH patients (39%) have not had a liver biopsy to confirm the diagnosis. A greater proportion of diagnosed NASH patients have metabolic syndrome parameters than what is reported in the literature (type-II diabetes mellitus 54%, Obesity 71%, metabolic syndrome 59%). 82% of physicians use a lower threshold value to define significant alcohol consumption compared with practice guideline recommendations. 88% of physicians prescribe some form of pharmacologic treatment for NASH (Vit E: prescribed to 53% of NASH patients, statins: 57%, metformin: 50%). Therefore, the vast majority of patients are prescribed medications despite a lack of a confirmed diagnosis or significant data to support the intervention and alcohol thresholds to exclude NASH are lower than expected.

Another common liver disease is primary sclerosing cholangitis (PSC). It is a chronic or long-term liver disease that slowly damages the bile ducts inside and outside the liver. In patients with PSC, bile accumulates in the liver due to blocked bile ducts, where it gradually damages liver cells and causes cirrhosis, or scarring of the liver. Currently, there is no effective treatment to cure PSC. Many patients having PSC ultimately need a liver transplant due to liver failure, typically about 10 years after being diagnosed with the disease. PSC may also lead to bile duct cancer.

Liver fibrosis is the excessive accumulation of extracellular matrix proteins, including collagen, that occurs in most types of chronic liver diseases. Advanced liver fibrosis results in cirrhosis, liver failure, and portal hypertension and often requires liver transplantation.

Methods

Disclosed herein is a method of treating and/or preventing liver disease in a patient in need thereof, comprising administering to the patient a therapeutically effective amount of an ASK1 inhibitor in combination with a therapeutically effective amount of a FXR agonist. The presence of active liver disease can be detected by the existence of elevated enzyme levels in the blood. Specifically, blood levels of alanine aminotransferase (ALT) and aspartate aminotransferase (AST), above clinically accepted normal ranges, are known to be indicative of on-going liver damage. Routine monitoring of liver disease patients for blood levels of ALT and AST is used clinically to measure progress of the liver disease while on medical treatment. Reduction of elevated ALT and AST to within the accepted normal range is taken as clinical evidence reflecting a reduction in the severity of the patients on-going liver damage.

In certain embodiments, the liver disease is a chronic liver disease. Chronic liver diseases involve the progressive destruction and regeneration of the liver parenchyma, leading to fibrosis and cirrhosis. In general, chronic liver diseases can be caused by viruses (such as hepatitis B, hepatitis C, cytomegalovirus (CMV), or Epstein Barr Virus (EBV)), toxic agents or drugs (such as alcohol, methotrexate, or nitrofurantoin), a metabolic disease (such as non-alcoholic fatty liver disease (NAFLD), non-alcoholic steatohepatitis (NASH), haemochromatosis, or Wilson's Disease), an autoimmune disease (such as Autoimmune Chronic Hepatitis, Primary Biliary Cirrhosis, or Primary Sclerosing Cholangitis), or other causes (such as right heart failure).

In one embodiment, provided herein is a method for reducing the level of cirrhosis. In one embodiment, cirrhosis is characterized pathologically by loss of the normal microscopic lobular architecture, with fibrosis and nodular regeneration. Methods for measuring the extent of cirrhosis are well known in the art. In one embodiment, the level of cirrhosis is reduced by about 5% to about 100%. In one embodiment, the level of cirrhosis is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% in the subject.

In certain embodiments, the liver disease is a metabolic liver disease. In one embodiment, the liver disease is non-alcoholic fatty liver disease (NAFLD). NAFLD is associated with insulin resistance and metabolic syndrome (obesity, combined hyperlipidemia, diabetes mellitus (type II) and high blood pressure). NAFLD is considered to cover a spectrum of disease activity, and begins as fatty accumulation in the liver (hepatic steatosis).

It has been shown that both obesity and insulin resistance probably play a strong role in the disease process of NAFLD. In addition to a poor diet, NAFLD has several other known causes. For example, NAFLD can be caused by certain medications, such as amiodarone, antiviral drugs (e.g., nucleoside analogues), aspirin (rarely as part of Reye's syndrome in children), corticosteroids, methotrexate, tamoxifen, or tetracycline. NAFLD has also been linked to the consumption of soft drinks through the presence of high fructose corn syrup which may cause increased deposition of fat in the abdomen, although the consumption of sucrose shows a similar effect (likely due to its breakdown into fructose). Genetics has also been known to play a role, as two genetic mutations for this susceptibility have been identified.

If left untreated, NAFLD can develop into non-alcoholic steatohepatitis (NASH), which is the most extreme form of NAFLD, a state in which steatosis is combined with inflammation and fibrosis. NASH is regarded as a major cause of cirrhosis of the liver of unknown cause. Accordingly, provided herein is a method of treating and/or preventing nonalcoholic steatohepatitis (NASH) in a patient in need thereof, comprising administering to the patient a therapeutically effective amount of an ASK1 inhibitor in combination with a therapeutically effective amount of a FXR agonist.

Also provided herein is a method of treating and/or preventing liver fibrosis in a patient in need thereof, comprising administering to the patient a therapeutically effective amount of an ASK1 inhibitor in combination with a therapeutically effective amount of a FXR agonist. Liver fibrosis is the excessive accumulation of extracellular matrix proteins including collagen that occurs in most types of chronic liver diseases. In certain embodiments, advanced liver fibrosis results in cirrhosis and liver failure. Methods for measuring liver histologies, such as changes in the extent of fibrosis, lobular hepatitis, and periportal bridging necrosis, are well known in the art.

In one embodiment, the level of liver fibrosis, which is the formation of fibrous tissue, fibroid or fibrous degeneration, is reduced by more that about 90%. In one embodiment, the level of fibrosis, which is the formation of fibrous tissue, fibroid or fibrous degeneration, is reduced by at least about 90%, at least about 80%, at least about 70%, at least about 60%, at least about 50%, at least about 40%, at least about 30%, at least about 20%, at least about 10%, at least about 5% or at least about 2%.

In one embodiment, the compounds provided herein reduce the level of fibrogenesis in the liver. Liver fibrogenesis is the process leading to the deposition of an excess of extracellular matrix components in the liver known as fibrosis. It is observed in a number of conditions such as chronic viral hepatitis B and C, alcoholic liver disease, drug-induced liver disease, hemochromatosis, auto-immune hepatitis, Wilson disease, primary biliary cirrhosis, sclerosing cholangitis, liver schistosomiasis and others. In one embodiment, the level of fibrogenesis is reduced by more that about 90%. In one embodiment, the level of fibrogenesis is reduced by at least about 90%, at least about 80%, at least about 70%, at least about 60%, at least about 50%, at least about 40%, at least about 30%, at least about 20%, at least about 10%, at least about 5% or at least about 2%.

In still other embodiments, provided herein is a method of treating and/or preventing primary sclerosing cholangitis (PSC) in a patient in need thereof, comprising administering to the patient a therapeutically effective amount of an ASK1 inhibitor in combination with a therapeutically effective amount of a FXR agonist.

ASK1 Inhibitors

An ASK1 inhibitor for use in the methods and pharmaceutical compositions disclosed herein may be any chemical compound or biological molecule (e.g., a protein or antibody) capable of inactivating apoptosis signal regulating kinase 1 (ASK1) protein. ASK1 inhibitors for use in the methods described herein are known (see, e.g., U.S. Patent Application Publication Nos. 2011/0009410, 2013/0197037, 2013/0197037, 2014/0179663, and 2014/0018370, all of which are incorporated herein by reference in their entirety) and/or can be identified via known methods (see, e.g., U.S. Patent Application Publication Nos. 2007/0276050 and 2011/0009410, which are incorporated herein by reference in their entirety).

In certain embodiments, the ASK1 inhibitor is a compound having the structure of formula (I):

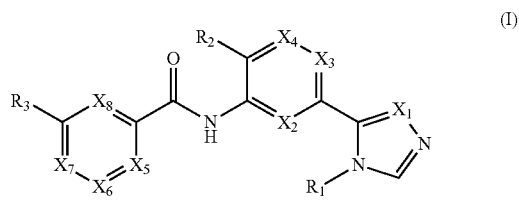

wherein:

$R^1$ is alkyl, alkenyl, alkynyl, cycloalkyl, aryl, heteroaryl, or heterocyclyl, wherein the alkyl, alkenyl, alkynyl, cycloalkyl, aryl, heteroaryl, and heterocyclyl are optionally substituted with from one to three substituents selected from halo, oxo, alkyl, cycloalkyl, heterocyclyl, aryl, aryloxy, —$NO_2$, $R^6$, —C(O)—$R^6$, —OC(O)—$R^6$—C(O)—O—$R^6$, C(O)—N($R^6$)($R^7$), —OC(O)—N($R^6$)($R^7$), —S—$R^6$, —S(=O)—$R^6$, —S(=O)$_2R^6$, —S(=O)$_2$—N($R^6$)($R^7$), —S(=O)$_2$—O—$R^6$, —N($R^6$)($R^7$), —N($R^6$)—C(O)—$R^7$, —N($R^6$)—C(O)—O—$R^7$, —N($R^6$)—C(O)—N($R^6$)($R^7$), —N($R^6$)—S(=O)$_2$—$R^6$, —CN, and —O—$R^6$, and wherein the alkyl, cycloalkyl, heterocyclyl, phenyl, and phenoxy are optionally substituted by from one to three substituents selected from alkyl, cycloalkyl, alkoxy, hydroxyl, and halo; wherein $R^6$ and $R^7$ are independently selected from the group consisting of hydrogen, alkyl, cycloalkyl, heterocyclyl, aryl, and heteroaryl, all of which are optionally substituted with from one to three substituents selected from halo, alkyl, monoalkylamino, dialkylamino, alkyl amide, aryl amide, heteroaryl amide, —CN, lower alkoxy, —$CF_3$, aryl, and heteroaryl; or $R^6$ and $R^7$ when taken together with the nitrogen to which they are attached form a heterocycle;

$R^2$ is hydrogen, halo, cyano, alkoxy, or alkyl optionally substituted by halo;

$R^3$ is aryl, heteroaryl, or heterocyclyl, wherein the aryl, heteroaryl, and heterocyclyl are optionally substituted with from one to five substituents selected from alkyl, alkoxy, cycloalkyl, cycloalkylalkyl, aryl, arylalkyl, heteroaryl, heteroarylalkyl, heterocyclyl, heterocyclylalkyl, halo, oxo, —$NO_2$, haloalkyl, haloalkoxy, —CN, —O—$R^6$, —O—C(O)—$R^6$, —O—C(O)—N($R^6$)($R^7$), —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—$R^6$, —C(O)—N($R^6$)($R^7$), and —N($R^6$)—S(=O)$_2$—$R^7$, wherein the alkyl, alkoxy, cycloalkyl, aryl, heteroaryl or heterocyclyl is optionally substituted with from one to five substituents selected from halo, oxo, —$NO_2$, alkyl, haloalkyl, haloalkoxy, —N($R^6$)($R^7$), —C(O)—$R^6$, —C(O)—O—$R^6$, —C(O)—N($R^6$)($R^7$), —CN, —O—$R^6$, cycloalkyl, aryl, heteroaryl and heterocyclyl; with the proviso that the heteroaryl or heterocyclyl moiety includes at least one ring nitrogen atom;

$X^1$, $X^2$, $X^3$, $X^4$, $X^5$, $X^6$, $X^7$ and $X^8$ are independently C($R^4$) or N, in which each $R^4$ is independently hydrogen, alkyl, alkoxy, cycloalkyl, aryl, heteroaryl, heterocyclyl, halo, —$NO_2$, haloalkyl, haloalkoxy, —CN, —O—$R^6$, —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C (O)—R⁷, —N(R⁶)—C(O)—O—R⁷, —N(R⁶)—C(O)—N(R⁶)(R⁷), —C(O)—R⁶, —C(O)—O—R⁶, —C(O)—N(R⁶)(R⁷), or —N(R⁶)—S(=O)₂—R⁷, wherein the alkyl, cycloalkyl, aryl, heteroaryl, and heterocyclyl is further optionally substituted with from one to five substituents selected from halo, oxo, —NO₂, —CF₃, —O—CF₃, —N(R⁶)(R⁷), —C(O)—R⁶, —C(O)—O—R⁷, —C(O)—N(R⁶)(R⁷), —CN, —O—R⁶; or X⁵ and X⁶ or X⁶ and X⁷ are joined to provide optionally substituted fused aryl or optionally substituted fused heteroaryl; and with the proviso that at least one of X², X³, and X⁴ is C(R⁴); at least two of X⁵, X⁶, X⁷, and X⁸ are C(R⁴); and at least one of X², X³, X⁴, X⁵, X⁶, X⁷ and X⁸ is N;

or a pharmaceutically acceptable salt, isomer, or a mixture thereof.

In certain embodiments, the compound of formula (I) has the structure of formula (IA):

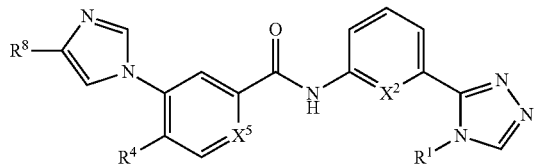

(IA)

wherein:

R¹ is alkyl, alkenyl, alkynyl, cycloalkyl, aryl, heteroaryl, or heterocyclyl, wherein the alkyl, alkenyl, alkynyl, cycloalkyl, aryl, heteroaryl, and heterocyclyl are optionally substituted with from one to three substituents selected from halo, oxo, alkyl, cycloalkyl, heterocyclyl, aryl, aryloxy, —NO₂, R⁶, —C(O)—R⁶, —OC(O)—R⁶—C(O)—O—R⁶, C(O)—N(R⁶)(R⁷), —OC(O)—N(R⁶)(R⁷), —S—R⁶, —S(=O)—R⁶, —S(=O)₂R⁶, —S(=O)₂—N(R⁶)(R⁷), —S(=O)₂—O—R⁶, —N(R⁶)(R⁷), —N(R⁶)—C(O)—R⁷, —N(R⁶)—C(O)—O—R⁷, —N(R⁶)—C(O)—N(R⁶)(R⁷), —N(R⁶)—S(=O)₂—R⁶, —CN, and —O—R⁶, and wherein the alkyl, cycloalkyl, heterocyclyl, phenyl, and phenoxy are optionally substituted by from one to three substituents selected from alkyl, cycloalkyl, alkoxy, hydroxyl, and halo; wherein R⁶ and R⁷ are independently selected from the group consisting of hydrogen, alkyl, cycloalkyl, heterocyclyl, aryl, and heteroaryl, all of which are optionally substituted with from one to three substituents selected from halo, alkyl, monoalkylamino, dialkylamino, alkyl amide, aryl amide, heteroaryl amide, —CN, lower alkoxy, —CF₃, aryl, and heteroaryl; or R⁶ and R⁷ when taken together with the nitrogen to which they are attached form a heterocycle;

R⁸ is hydrogen, alkyl, alkoxy, cycloalkyl, cycloalkylalkyl, aryl, arylalkyl, heteroaryl, heteroarylalkyl, heterocyclyl, heterocyclylalkyl, halo, oxo, —NO₂, haloalkyl, haloalkoxy, —CN, —O—R⁶, —O—C(O)—R⁶, —O—C(O)—N(R⁶)(R⁷), —S—R⁶, —N(R⁶)(R⁷), —S(=O)—R⁶, —S(=O)₂R⁶, —S(=O)₂—N(R⁶)(R⁷), —S(=O)₂—O—R⁶, —N(R⁶)—C(O)—R⁷, —N(R⁶)—C(O)—O—R⁷, —N(R⁶)—C(O)—N(R⁶)(R⁷), —C(O)—R⁶, —C(O)—O—R⁶, —C(O)—N(R⁶)(R⁷), and —N(R⁶)—S(=O)₂—R⁷, wherein the alkyl, alkoxy, cycloalkyl, aryl, heteroaryl or heterocyclyl is optionally substituted with from one to five substituents selected from halo, oxo, —NO₂, alkyl, haloalkyl, haloalkoxy, —N(R⁶)(R⁷), —C(O)—R⁶, —C(O)—O—R⁷, —C(O)—N(R⁶)(R⁷), —CN, —O—R⁶, cycloalkyl, aryl, heteroaryl and heterocyclyl; with the proviso that the heteroaryl or heterocyclyl moiety includes at least one ring nitrogen atom;

X² and X⁵ are independently C(R⁴) or N; and each R⁴ is independently hydrogen, alkyl, alkoxy, cycloalkyl, aryl, heteroaryl, heterocyclyl, halo, —NO₂, haloalkyl, haloalkoxy, —CN, —O—R⁶, —S—R⁶, —N(R⁶)(R⁷), —S(=O)—R⁶, —S(=O)₂R⁶, —S(=O)₂—N(R⁶)(R⁷), —S(=O)₂—O—R⁶, —N(R⁶)—C(O)—R⁷, —N(R⁶)—C(O)—O—R⁷, —N(R⁶)—C(O)—N(R⁶)(R⁷), —C(O)—R⁶, —C(O)—O—R⁶, —C(O)—N(R⁶)(R⁷), or —N(R⁶)—S(=O)₂—R⁷, wherein the alkyl, cycloalkyl, aryl, heteroaryl, and heterocyclyl is further optionally substituted with from one to five substituents selected from halo, oxo, —NO₂, —CF₃, —O—CF₃, —N(R⁶)(R⁷), —C(O)—R⁶, —C(O)—O—R⁷, —C(O)—N(R⁶)(R⁷), —CN, and —O—R⁶;

with the proviso that at least one of X² and X⁵ is N;

or a pharmaceutically acceptable salt, isomer, or a mixture thereof.

Exemplary compounds of Formula (I) and (IA) for use in the methods and pharmaceutical compositions described herein can be found in U.S. Patent Application Publication No. 2011/0009410, which is incorporated herein by reference in its entirety.

In certain embodiments, the ASK1 inhibitor is a compound of formula (II):

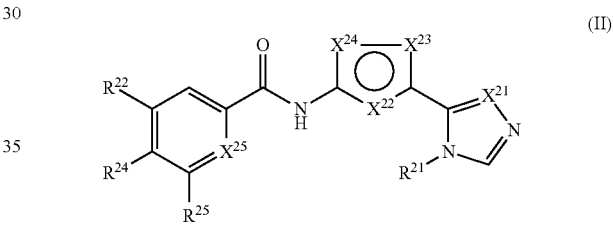

(II)

wherein:

R²¹ is alkyl, alkenyl, alkynyl, cycloalkyl, aryl, heteroaryl, or heterocyclyl, wherein the alkyl, alkenyl, alkynyl, cycloalkyl, aryl, heteroaryl, and heterocyclyl are optionally substituted with from one to four substituents selected from the group consisting of halo, hydroxyl, oxo, alkyl, cycloalkyl, heterocyclyl, aryl, aryloxy, NO₂, R²⁶, C(O)R²⁶, OC(O)R²⁶C(O)OR²⁶, C(O)N(R²⁶)(R²⁷), OC(O)N(R²⁶)(R²⁷), SR²⁶, S(=O)R²⁶, S(=O)₂R²⁶, S(=O)₂N(R²⁶)(R²⁷), S(=O)₂OR²⁶, N(R²⁶)(R²⁷), N(R²⁶)C(O)R²⁷, N(R²⁶)C(O)OR²⁷, N(R²⁶)C(O)N(R²⁶)(R²⁷), N(R²⁶)S(=O)₂R²⁶, CN, and OR²⁶, wherein the alkyl, cycloalkyl, heterocyclyl, aryl, and aryloxy are optionally substituted with from one to three substituents selected from alkyl, cycloalkyl, alkoxy, hydroxyl, and halo;

R²⁶ and R²⁷ are independently selected from the group consisting of hydrogen, alkyl, cycloalkyl, heterocyclyl, aryl, and heteroaryl, wherein the alkyl, cycloalkyl, heterocyclyl, aryl, and heteroaryl are optionally substituted with from one to three substituents selected from halo, alkyl, monoalkylamino, dialkylamino, alkyl amide, aryl amide, heteroaryl amide, CN, lower alkoxy, CF₃, aryl, and heteroaryl; or R²⁶ and R²⁷ when taken together with the nitrogen to which they are attached form a heterocycle;

R²² is aryl, heteroaryl, or heterocyclyl, wherein the aryl, heteroaryl, and heterocyclyl are optionally substituted with from one to five substituents selected from alkyl, alkoxy, cycloalkyl, cycloalkylalkyl, aryl, arylalkyl, heteroaryl, heteroarylalkyl, heteroaryl, heterocyclyl, heterocyclylalkyl, halo, oxo, NO$_2$, haloalkyl, haloalkoxy, CN, OR$^{26}$, OC(O)R$^{26}$, OC(O)N(R$^{26}$)(R$^{27}$), SR$^{26}$, N(R$^{26}$)(R$^{27}$), S(=O)R$^{26}$, S(=O)$_2$R$^{26}$, S(=O)$_2$N(R$^{26}$)(R$^{27}$), S(=O)$_2$OR$^{26}$, N(R$^{26}$)C(O)R$^{27}$, N(R$^{26}$)C(O)OR$^{27}$, N(R$^{26}$)C(O)N(R$^{26}$)(R$^{27}$), C(O)R$^{26}$, C(O)OR$^{26}$, C(O)N(R$^{26}$)(R$^{27}$), and N(R$^{26}$)S(=O)$_2$R$^{27}$, and wherein the alkyl, alkoxy, cycloalkyl, aryl, heteroaryl and heterocyclyl are optionally substituted with one or more substituents selected from halo, oxo, NO$_2$, alkyl, haloalkyl, haloalkoxy, N(R$^{26}$)(R$^{27}$), C(O)R$^{26}$, C(O)OR$^{26}$, C(O)N(R$^{26}$)(R$^{27}$), CN, OR$^{26}$, cycloalkyl, aryl, heteroaryl and heterocyclyl; with the proviso that the heteroaryl or heterocyclyl moiety includes at least one ring nitrogen atom;

R$^{24}$ and R$^{25}$ are independently hydrogen, halo, cyano, alkyl, alkoxy, or cycloalkyl, wherein the alkyl, alkoxy, and cycloalkyl are optionally substituted by halo or cycloalkyl;

X$^{21}$ and X$^{25}$ are independently C(R$^{23}$) or N, wherein each R$^{23}$ is independently hydrogen, halo, alkyl, alkoxy or cycloalkyl, wherein the alkyl and cycloalkyl are optionally substituted with from one to five substituents selected from halo, oxo, CF$_3$, OCF$_3$, N(R$^{26}$)(R$^{27}$), C(O)R$^{26}$, C(O)OR$^{27}$, C(O)N(R$^{26}$)(R$^{27}$), CN, and OR$^{26}$; and X$^{22}$, X$^{23}$ and X$^{24}$ are independently C(R$^{23}$), N, O, or S; with the proviso that at least one of X$^{22}$, X$^{23}$, and X$^{24}$ is C(R$^{23}$); and only one of X$^{22}$, X$^{23}$, and X$^{24}$ is O or S;

or a pharmaceutically acceptable salt, isomer, or a mixture thereof.

In some embodiment, the ASK1 inhibitor is the compound having the structure of formula (II), wherein:

R$^{21}$ is C$_{1-6}$ alkyl, C$_{2-6}$ alkenyl, C$_{2-6}$ alkynyl, C$_{3-6}$ cycloalkyl, aryl, heteroaryl, or heterocyclyl, wherein the C$_{1-6}$ alkyl, C$_{2-6}$ alkenyl, C$_{2-6}$ alkynyl, C$_{3-6}$ cycloalkyl, aryl, heteroaryl, and heterocyclyl are optionally substituted with from one to four substituents selected from the group consisting of halo, hydroxyl, oxo, alkyl, cycloalkyl, heterocyclyl, aryl, aryloxy, NO$_2$, R$^{26}$, C(O)R$^{26}$, OC(O)R$^{26}$C(O)OR$^{26}$, C(O)N(R$^{26}$)(R$^{27}$), OC(O)N(R$^{26}$)(R$^{27}$), SR$^{26}$, S(=O)R$^{26}$, S(=O)$_2$R$^{26}$, S(=O)$_2$N(R$^{26}$)(R$^{27}$), S(=O)$_2$OR$^{26}$, N(R$^{26}$)(R$^{27}$), N(R$^{26}$)C(O)R$^{27}$, N(R$^{26}$)C(O)OR$^{27}$, N(R$^{26}$)C(O)N(R$^{26}$)(R$^{27}$), N(R$^{26}$)S(=O)$_2$R$^{26}$, CN, and OR$^{26}$, wherein the alkyl, cycloalkyl, heterocyclyl, aryl, and aryloxy are optionally substituted with from one to three substituents selected from alkyl, cycloalkyl, alkoxy, hydroxyl, and halo;

R$^{26}$ and R$^{27}$ are independently selected from the group consisting of hydrogen, alkyl, cycloalkyl, heterocyclyl, aryl, and heteroaryl, wherein the alkyl, cycloalkyl, heterocyclyl, aryl, and heteroaryl are optionally substituted with from one to three substituents selected from halo, alkyl, monoalkylamino, dialkylamino, alkyl amide, aryl amide, heteroaryl amide, CN, lower alkoxy, CF$_3$, aryl, and heteroaryl; or R$^{26}$ and R$^{27}$ when taken together with the nitrogen to which they are attached form a heterocycle;

R$^{22}$ is aryl, heteroaryl, or heterocyclyl, wherein the aryl, heteroaryl, and heterocyclyl are optionally substituted with from one to five substituents selected from alkyl, alkoxy, cycloalkyl, cycloalkylalkyl, aryl, arylalkyl, heteroaryl, heteroarylalkyl, heterocyclyl, heterocyclylalkyl, halo, oxo, NO$_2$, haloalkyl, haloalkoxy, CN, OR$^{26}$, OC(O)R$^{26}$, OC(O)N(R$^{26}$)(R$^{27}$), SR$^{26}$, N(R$^{26}$)(R$^{27}$), S(=O)R$^{26}$, S(=O)$_2$R$^{26}$, S(=O)$_2$N(R$^{26}$)(R$^{27}$), S(=O)$_2$OR$^{26}$, N(R$^{26}$)C(O)R$^{27}$, N(R$^{26}$)C(O)OR$^{27}$, N(R$^{26}$)C(O)N(R$^{26}$)(R$^{27}$), C(O)R$^{26}$, C(O)OR$^{26}$, C(O)N(R$^{26}$)(R$^{27}$), and N(R$^{26}$)S(=O)$_2$R$^{27}$, and wherein the alkyl, alkoxy, cycloalkyl, aryl, heteroaryl and heterocyclyl are optionally substituted with one or more substituents selected from halo, oxo, NO$_2$, alkyl, haloalkyl, haloalkoxy, N(R$^{26}$)(R$^{27}$), C(O)R$^{26}$, C(O)OR$^{26}$, C(O)N(R$^{26}$)(R$^{27}$), CN, OR$^{26}$, cycloalkyl, aryl, heteroaryl and heterocyclyl; with the proviso that the heteroaryl or heterocyclyl moiety includes at least one ring nitrogen atom;

R$^{24}$ and R$^{25}$ are independently hydrogen, halo, cyano, C$_{1-6}$ alkyl, C$_{1-6}$ alkoxy, or C$_{1-6}$ cycloalkyl, wherein the alkyl, alkoxy, and cycloalkyl are optionally substituted by halo or C$_{3-8}$ cycloalkyl;

X$^{21}$ and X$^{25}$ are independently C(R$^{23}$) or N, wherein each R$^{23}$ is independently hydrogen, halo, C$_{1-6}$ alkyl, C$_{1-6}$ alkoxy or C$_{3-8}$ cycloalkyl, wherein the alkyl and cycloalkyl are optionally substituted with from one to five substituents selected from halo, oxo, CF$_3$, OCF$_3$, N(R$^{26}$)(R$^{27}$), C(O)R$^{26}$, C(O)OR$^{27}$, C(O)N(R$^{26}$)(R$^{27}$), CN, and OR$^{26}$; and X$^{22}$, X$^{23}$ and X$^{24}$ are independently C(R$^{23}$), N, O, or S; with the proviso that at least one of X$^{22}$, X$^{23}$, and X$^{24}$ is C(R$^{23}$); and only one of X$^{22}$, X$^{23}$, and X$^{24}$ is O or S;

or a pharmaceutically acceptable salt, isomer, or a mixture thereof.

Exemplary compounds of Formula (II) for use in the methods and pharmaceutical compositions described herein can be found in U.S. Patent Application Publication No. 2012/0004267, which is incorporated herein by reference in its entirety.

In certain embodiments, the ASK1 inhibitor is a compound of formula (III):

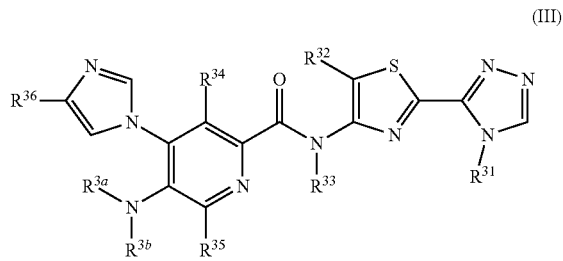

wherein:

R$^{31}$ is alkyl or cycloalkyl, wherein the alkyl or cycloalkyl is optionally substituted with one to three halogen atoms;

R$^{32}$ is hydrogen or alkyl wherein the alkyl is optionally substituted with halo.

R$^{33}$ is hydrogen or alkyl;

R$^{34}$ is hydrogen or alkyl;

R$^{35}$ is hydrogen, alkyl, OR$^{3a}$ or —NHR$^{3a}$;

R$^{36}$ is hydrogen, alkyl, haloalkyl, or C$_3$-C$_6$ cycloalkyl wherein the cycloalkyl is optionally substituted with alkyl, haloalkyl, or 1 or 2 halogen atoms;

R$^{3a}$ and R$^{3b}$ are independently hydrogen, alkyl or R$^{3a}$ and R$^{3b}$ combine with the nitrogen atom to which they are attached to form a four to six member heterocyclic ring optionally containing an oxygen or a nitrogen atom in the ring;

or a pharmaceutically acceptable salt, isomer, or mixture thereof.

In certain embodiment, the ASK1 inhibitor is a compound having the structure of formula (III), wherein:

R$^{31}$ is C$_1$-C$_3$ alkyl or C$_3$-C$_6$ cycloalkyl, wherein the alkyl or cycloalkyl is optionally substituted with one to three halogen atoms;

R$^{32}$ is hydrogen or C$_1$-C$_6$ alkyl wherein the alkyl is optionally substituted with halo.

R$^{33}$ is hydrogen or C$_1$-C$_3$ alkyl;

R$^{34}$ is hydrogen or C$_1$-C$_3$ alkyl;

R$^{35}$ is hydrogen, C$_1$-C$_3$ alkyl, OR$^{3a}$ or —NHR$^{3a}$;

$R^{36}$ is hydrogen, $C_1$-$C_3$ alkyl, $C_1$-$C_3$ haloalkyl, or $C_3$-$C_6$ cycloalkyl wherein the cycloalkyl is optionally substituted with $C_1$-$C_3$ alkyl, $C_1$-$C_3$ haloalkyl, or 1 or 2 halogen atoms;

$R^{3a}$ and $R^{3b}$ are independently hydrogen, $C_1$-$C_3$ alkyl or $R^{3a}$ and $R^{3b}$ combine with the nitrogen atom to which they are attached to form a four to six member heterocyclic ring optionally containing an oxygen or a nitrogen atom in the ring;

or a pharmaceutically acceptable salt, isomer, or mixture thereof.

Exemplary compounds of Formula (III) for use in the methods and pharmaceutical compositions described herein can be found in U.S. Patent Application Publication No. 2014/0179663, which is incorporated herein by reference in its entirety.

In some embodiments, the ASK 1 inhibitor are the compounds described in U.S. Patent Application Publication Nos. 2007/0276050, 2011/0009410, 2013/0197037, 2013/0197037, and 2014/0179663, 2014/0038957, 2014/0018370, 2009/0318425, 2011/0077235, 2012/0316194, U.S. Pat. No. 8,263,595, U.S. Provisional Patent Application No. 61/918,784, and PCT Patent Application Publication No. 2011/041293; all of which are incorporated herein by reference in their entirety. In certain embodiments, the ASK1 inhibitor is:

(Compound 1)
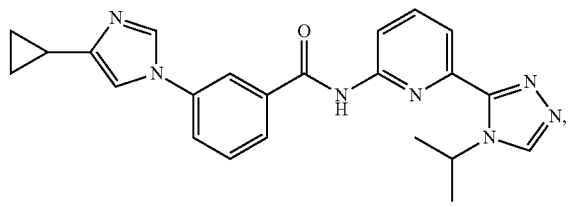 [SMILES: CC(C)n1cnnc1-c1cccc(NC(=O)c2cccc(-n3cnc(C4CC4)c3)c2)n1]

(Compound 2)
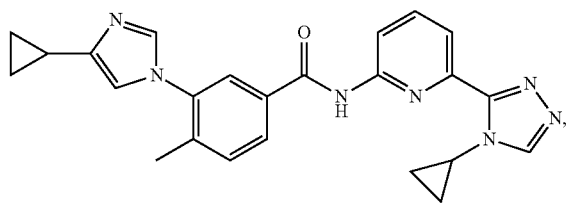

(Compound 3)
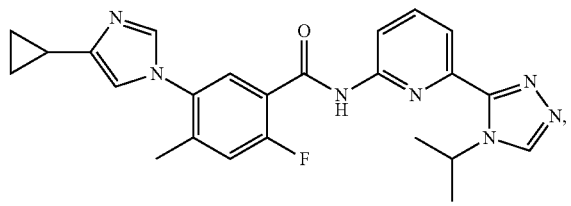

(Compound 4)
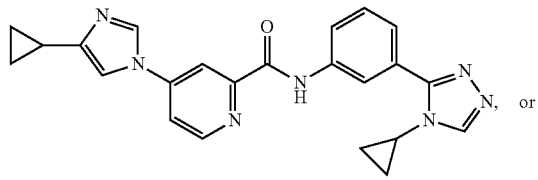

or (Compound 5)
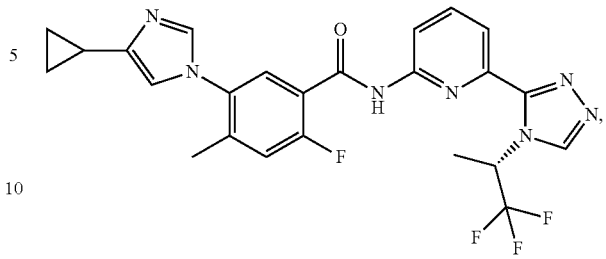

or a pharmaceutically acceptable salt, isomer, or a mixture thereof. Compounds 1, 2, 3, 4, and 5 may be synthesized and characterized using the commonly used methods or those described in U.S. Patent Application Publication Nos. 2011/0009410 and 2013/0197037. In one embodiment, the ASK1 inhibitor is Compound 1 or a pharmaceutically acceptable salt thereof. In some embodiment, the ASK1 inhibitor is Compound 2 or a pharmaceutically acceptable salt thereof. In further embodiment, the ASK1 inhibitor is Compound 3 or a pharmaceutically acceptable salt thereof. In some further embodiment, the ASK1 inhibitor is Compound 4 or a pharmaceutically acceptable salt thereof. In certain further embodiment, the ASK1 inhibitor is Compound 5 or a pharmaceutically acceptable salt thereof.

The compounds of the present application may be represented by structures or chemical names. Also, the compounds may be named using the nomenclature systems and symbols that are commonly recognized in the art of chemistry including; for example, ChemBioDraw Ultra 12.0, Chemical Abstract Service (CAS), and International Union of Pure and Applied Chemistry (IUPAC). By way of example, Compound 3 may also be referred to as 5-(4-cyclopropyl-1H-imidazol-1-yl)-N-(6-(4-isopropyl-4H-1,2,4-triazol-3-yl)pyridin-2-yl)-2-fluoro-4-methylbenzamide, 5-(4-cyclopropylimidazol-1-yl)-2-fluoro-4-methyl-N-[6-(4-propan-2-yl-1,2,4-triazol-3-yl)pyridin-2-yl]benzamide, or 5-(4-cyclopropyl-1H-imidazol-1-yl)-2-fluoro-N-(6-(4-isopropyl-4H-1,2,4-triazol-3-yl)pyridin-2-yl)-4-methylbenzamide. Unless stated otherwise, the compounds described herein are named using ChemBioDraw Ultra 12.0; accordingly, Compound 1 may be referred to as 3-(4-cyclopropyl-1H-imidazol-1-yl)-N-(6-(4-isopropyl-4H-1,2,4-triazol-3-yl)pyridin-2-yl)benzamide, Compound 2 may be referred to as 3-(4-cyclopropyl-1H-imidazol-1-yl)-N-(6-(4-cyclopropyl-4H-1,2,4-triazol-3-yl)pyridin-2-yl)-4-methylbenzamide, Compound 3 may be referred to as 5-(4-cyclopropyl-1H-imidazol-1-yl)-2-fluoro-N-(6-(4-isopropyl-4H-1,2,4-triazol-3-yl)pyridin-2-yl)-4-methylbenzamide, Compound 4 may be referred to as 4-(4-cyclopropyl-1H-imidazol-1-yl)-N-(3-(4-cyclopropyl-4H-1,2,4-triazol-3-yl)phenyl)picolinamide, and Compound 5 may be referred to as (S)-5-(4-cyclopropyl-1H-imidazol-1-yl)-2-fluoro-4-methyl-N-(6-(4-(1,1,1-trifluoropropan-2-yl)-4H-1,2,4-triazol-3-yl)pyridin-2-yl)benzamide.

FXR Agonist

Farnesoid X receptors are known to be expressed in liver, intestine, kidney and adrenal tissues. Activated FXR translocates to the cell nucleus and forms a heterodimer with retinoid X receptor (RXR). The dimer binds to hormone response elements on DNA causing, among other effects, a suppression of cholesterol 7 alpha-hydroxylase (CYP7A1), the rate-limiting enzyme in bile acid synthesis from cholesterol, and stimulation of intestinal bile acid binding protein (IBABP). Both CYP7A1 and IBABP are involved in homeostatis of bile acid and cholesterol. A FXR agonist for use in the methods and pharmaceutical compositions disclosed herein may be any chemical compound or biological molecule (e.g., a protein or antibody) capable of binding and activating FXR. For example, GW4064 (3-(2,6-Dichlorophenyl)-4-(3'-carboxy-2-chlorostilben-4-yl)oxymethyl-5-isopropylisoxazole) and bile acids such as chenodeoxycholic acid (CDCA), lithocholic acid (LCA) and deoxycholic acid (DCA) are known to act as agonists of FXR. Additional examples of FXR agonist may be found in U.S. Publication Nos. 20100184809, 20100210660, 2012 0232116, 20140221659, 20140039007, 20140187633, 20140134262, and 20140057886. All publications cited in the application are incorporated by reference in their entirety.

It is suggested that FXR is a nuclear bile acid sensor that modulates the synthetic output of bile acids in the liver and their recycling in the intestine (by regulating bile acid binding proteins). Beyond bile acid physiology, FXR may be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as inflammatory bowel diseases or chronic intrahepatic forms of cholestasis and many others diseases (see Claudel et al., *Arteriosclerosis, Thrombosis, and Vascular Biology* 2005 vol. 25, No. 10, 2020-2030; Westin et al., *Mini Review Medicinal Chemistry* 2005 vol. 5, No. 8, 719-727).

FXR regulates a complex pattern of response genes in the liver. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or chenodeoxycholic acid (CDCA), this can be regarded as an example of feedback inhibition on the gene expression level (Goodwin et al., *Molecular Cell* 2000, vol. 6 No. 3, 517-526; Lu et al., *Molecular Cell* 2000, vol. 6, No. 3, 507-515). Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice (Sinai et al., *Cell* 2000, vol. 102, No. 6, 731-744) where under- or overexpression of several ABC-transporters in the liver was shown. Further detailed analysis revealed that the major bile salt excretory pump BSEP or ABCB11 (Ananthanarayanan et al., *Journal of Biological Chemistry* 2001, vol. 276, No. 31, 28857-28865; Plass et al., *Hepatology* 2002, vol. 35 No. 3, 589-96) as well as the key enzyme which mediates lipid transfer from lipoproteins to phospholipids, PLTP (Urizar et al., *Journal of Biological Chemisty* 2000, vol. 275, No. 50, 39313-39317), and the two key canalicular membrane transporters for phospholipids, MRP-2 (ABCC4) (Kast et al., *Journal of Biological Chemisty* 2002, vol. 277, No. 4, 2908-2915) and MDR-3 (ABCB4) (Huang et al., *Journal of Biological Chemisty* 2003, vol. 278, No. 51, 51085-51090) are direct targets for ligand-directed transcriptional activation by FXR (see Miyata, *Journal of Pharmacology and Experimental Therapeutics* 2005, vol. 312, No. 2, 759-766; Rizzo et al., *Current Drug Targets—Immune, Endocrine & Metabolic Disorders* 2005, vol. 5, No. 3, 289-303.).

Dosing and Administration

While it is possible for an active ingredient to be administered alone, it may be preferable to present them as pharmaceutical formulations or pharmaceutical compositions as described below. The formulations, both for veterinary and for human use, of the disclosure comprise at least one of the active ingredients, together with one or more acceptable carriers therefor and optionally other therapeutic ingredients. The carriers) must be "acceptable" in the sense of being compatible with the other ingredients of the formulation and physiologically innocuous to the recipient thereof.

Each of the active ingredients can be formulated with conventional carriers and excipients, which will be selected in accord with ordinary practice. Tablets can contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

The therapeutically effective amount of active ingredient can be readily determined by a skilled clinician using conventional dose escalation studies. Typically, the active ingredient will be administered in a dose from 0.01 milligrams to 2 grams. In one embodiment, the dosage will be from about 10 milligrams to 450 milligrams. In another embodiment, the dosage will be from about 25 to about 250 milligrams. In another embodiment, the dosage will be about 50 or 100 milligrams. In one embodiment, the dosage will be about 100 milligrams. It is contemplated that the active ingredient may be administered once, twice or three times a day. Also, the active ingredient may be administered once or twice a week, once every two weeks, once every three weeks, once every four weeks, once every five weeks, or once every six weeks.

The pharmaceutical composition for the active ingredient can include those suitable for the foregoing administration routes. The formulations can conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations suitable for oral administration can be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste. In certain embodiments, the active ingredient may be administered as a subcutaneous injection.

A tablet can be made by compression or molding, optionally with one or more accessory ingredients. Compressed tablets can be prepared by compressing in a suitable machine the active ingredient in a free-flowing form such as a powder or granules, optionally mixed with a binder, lubricant, inert diluent, preservative, or surface active agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

The active ingredient can be administered by any route appropriate to the condition. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. In certain embodiments, the active ingredients are orally bioavailable and can therefore be dosed orally. In one embodiment, the patient is human.

When used in combination in the methods disclosed herein, the ASK1 inhibitor and the FXR agonist can be administered together in a single pharmaceutical composition or separately (either concurrently or sequentially) in more than one pharmaceutical composition. In certain embodiments, the ASK1 inhibitor and the FXR agonist are administered together. In other embodiments, the ASK1 inhibitor and the FXR agonist are administered separately. In some aspects, the ASK1 inhibitor is administered prior to the FXR agonist. In some aspects, the FXR agonist is administered prior to the ASK1 inhibitor. When administered separately, the ASK1 inhibitor and the FXR agonist can be administered to the patient by the same or different routes of delivery.

Pharmaceutical Compositions

The pharmaceutical compositions of the disclosure provide for an effective amount of an ASK1 inhibitor and an effective amount of a FXR agonist.

When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as, for example, calcium or sodium carbonate, lactose, lactose monohydrate, croscarmellose sodium, povidone, calcium or sodium phosphate; granulating and disintegrating agents, such as, for example, maize starch, or alginic acid; binding agents, such as, for example, cellulose, microcrystalline cellulose, starch, gelatin or acacia; and lubricating agents, such as, for example, magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as, for example, glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as, for example, peanut oil, liquid paraffin or olive oil.

Aqueous suspensions of the disclosure contain the active materials in admixture with excipients suitable for the manufacture of aqueous suspensions. Such excipients include a suspending agent, such as, for example, sodium carboxymethylcellulose, methylcellulose, hydroxypropyl methylcelluose, sodium alginate, polyvinylpyrrolidone, gum tragacanth and gum acacia, and dispersing or wetting agents such as, for example, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as, for example, ethyl or n-propyl p-hydroxy-benzoate, one or more coloring agents, one or more flavoring agents and one or more sweetening agents, such as, for example, sucrose or saccharin.

Oil suspensions may be formulated by suspending the active ingredient in a vegetable oil, such as, for example, arachis oil, olive oil, sesame oil or coconut oil, or in a mineral oil such as, for example, liquid paraffin. The oral suspensions may contain a thickening agent, such as, for example, beeswax, hard paraffin or cetyl alcohol. Sweetening agents, such as, for example, those set forth above, and flavoring agents may be added to provide a palatable oral preparation. These compositions may be preserved by the addition of an antioxidant such as, for example, ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as, for example, olive oil or arachis oil, a mineral oil, such as, for example, liquid paraffin, or a mixture of these. Suitable emulsifying agents include naturally-occurring gums, such as, for example, gum acacia and gum tragacanth, naturally occurring phosphatides, such as, for example, soybean lecithin, esters or partial esters derived from fatty acids and hexitol anhydrides, such as, for example, sorbitan monooleate, and condensation products of these partial esters with ethylene oxide, such as, for example, polyoxyethylene sorbitan monooleate. The emulsion may also contain sweetening and flavoring agents. Syrups and elixirs may be formulated with sweetening agents, such as, for example, glycerol, sorbitol or sucrose. Such formulations may also contain a demulcent, a preservative, a flavoring or a coloring agent.

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as, for example, a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as, for example, oleic acid may likewise be used in the preparation of injectables.

The amount of active ingredient that may be combined with the carrier material to produce a single dosage form will vary depending upon the host treated and the particular mode of administration, such as oral administration or subcutaneous injection. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. When formulated for subcutaneous administration, the formulation is typically administered about twice a month over a period of from about two to about four months.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations can be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In one embodiment, the ASK1 inhibitor and the FXR agonist may be administered together in a combination formulation or in separate pharmaceutical compositions, where each inhibitor may be formulated in any suitable dosage form. In certain embodiments, the methods provided herein comprise administering separately a pharmaceutical composition comprising an ASK1 inhibitor and a pharmaceutically acceptable carrier or excipient and a pharmaceutical composition comprising a FXR agonist and a pharmaceutically acceptable carrier or excipient. Combination formulations according to the present disclosure comprise an ASK1 inhibitor and a FXR agonist together with one or more pharmaceutically acceptable carriers or excipients and optionally other therapeutic agents. Combination formulations containing the active ingredient may be in any form suitable for the intended method of administration.

What is claimed is:

1. A method of treating or preventing nonalcoholic steatohepatitis (NASH) in a patient in need thereof, comprising administering to the patient a therapeutically effective amount of an ASK1 inhibitor in combination with a therapeutically effective amount of a FXR agonist, wherein the ASK1 inhibitor is a compound of formula (I):

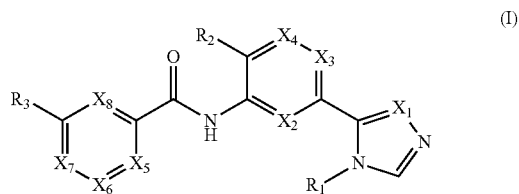

wherein:
$R^1$ is alkyl, alkenyl, alkynyl, cycloalkyl, aryl, heteroaryl, or heterocyclyl, wherein the alkyl, alkenyl, alkynyl, cycloalkyl, aryl, heteroaryl, and heterocyclyl are optionally substituted with from one to three substituents independently selected from halo, oxo, alkyl, cycloalkyl, heterocyclyl, aryl, aryloxy, —$NO_2$, $R^6$, —C(O)—$R^6$, —OC(O)—$R^6$—C(O)—O—$R^6$, C(O)—N($R^6$)($R^7$), —OC(O)—N($R^6$)($R^7$), —S—$R^6$, —S(=O)—$R^6$, —S(=O)$_2R^6$, —S(=O)$_2$—N($R^6$)($R^7$), —S(=O)$_2$—O—$R^6$, —N($R^6$)($R^7$), —N($R^6$)—C(O)—$R^7$, —N($R^6$)—C(O)—O—$R^7$, —N($R^6$)—C(O)—N($R^6$)($R^7$), —N($R^6$)—S(=O)$_2$—$R^6$, —CN, and —O—$R^6$, and wherein the alkyl, cycloalkyl, heterocyclyl, aryl, and aryloxy are optionally substituted by from one to three substituents independently selected from alkyl, cycloalkyl, alkoxy, hydroxyl, and halo; wherein $R^6$ and $R^7$ are independently selected from the group consisting of hydrogen, $C_1$-$C_{15}$ alkyl, cycloalkyl, heterocyclyl, aryl, and heteroaryl, all of which are optionally substituted with from one to three substituents independently selected from halo, alkyl, monoalkylamino, dialkylamino, alkyl amide, aryl amide, heteroaryl amide, —CN, lower alkoxy, —$CF_3$, aryl, and heteroaryl; or $R^6$ and $R^7$ when taken together with the nitrogen to which they are attached form a heterocycle;

$R^2$ is hydrogen, halo, cyano, alkoxy, or alkyl optionally substituted by halo;

$R^3$ is aryl, heteroaryl, or heterocyclyl, wherein the aryl, heteroaryl, and heterocyclyl are optionally substituted with from one to five substituents independently selected from alkyl, alkoxy, cycloalkyl, cycloalkylalkyl, aryl, arylalkyl, heteroaryl, heteroarylalkyl, heterocyclyl, heterocyclylalkyl, halo, oxo, —$NO_2$, haloalkyl, haloalkoxy, —CN, —O—$R^6$, —O—C(O)—$R^6$, —O—C(O)—N($R^6$)($R^7$), —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—$R^6$, —C(O)—N($R^6$)($R^7$), and —N($R^6$)—S(=O)$_2$—$R^7$, wherein the alkyl, alkoxy, cycloalkyl, aryl, heteroaryl or heterocyclyl is optionally substituted with from one to five substituents independently selected from halo, oxo, —$NO_2$, alkyl, haloalkyl, haloalkoxy, —N($R^6$)($R^7$), —C(O)—$R^6$, —C(O)—O—$R^6$, —C(O)—N($R^6$)($R^7$), —CN, —O—R⁶, cycloalkyl, aryl, heteroaryl and heterocyclyl; with the proviso that the heteroaryl or heterocyclyl moiety of R³ includes at least one ring nitrogen atom;

X¹, X², X³, X⁴, X⁵, X⁶, X⁷ and X⁸ are independently C(R⁴) or N, in which each R⁴ is independently hydrogen, alkyl, alkoxy, cycloalkyl, aryl, heteroaryl, heterocyclyl, halo, —NO₂, haloalkyl, haloalkoxy, —CN, —O—R⁶, —S—R⁶, —N(R⁶)(R⁷), —S(═O)—R⁶, —S(═O)₂R⁶, —S(═O)₂—N(R⁶)(R⁷), —S(═O)₂—O—R⁶, —N(R⁶)—C(O)—R⁷, —N(R⁶)—C(O)—O—R⁷, —N(R⁶)—C(O)—N(R⁶)(R⁷), —C(O)—R⁶, —C(O)—O—R⁶, —C(O)—N(R⁶)(R⁷), or —N(R⁶)—S(═O)₂—R⁷, wherein the alkyl, cycloalkyl, aryl, heteroaryl, and heterocyclyl is further optionally substituted with from one to five substituents independently selected from halo, oxo, —NO₂, —CF₃, —O—CF₃, —N(R⁶)(R⁷), —C(O)—R⁶, —C(O)—O—R⁷, —C(O)—N(R⁶)(R⁷), —CN, —O—R⁶; or X⁵ and X⁶ or X⁶ and X⁷ are joined to provide optionally substituted fused aryl or optionally substituted fused heteroaryl; and with the proviso that at least one of X², X³, and X⁴ is C(R⁴); at least two of X⁵, X⁶, X⁷, and X⁸ are C(R⁴); and at least one of X², X³, X⁴, X⁵, X⁶, X⁷ and X⁸ is N;

or a pharmaceutically acceptable salt, stereoisomer, or a mixture thereof.

2. A method of treating or preventing nonalcoholic steatohepatitis (NASH) in a patient in need thereof, comprising administering to the patient a therapeutically effective amount of an ASK1 inhibitor in combination with a therapeutically effective amount of a FXR agonist, wherein the ASK1 inhibitor is a compound of formula (II):

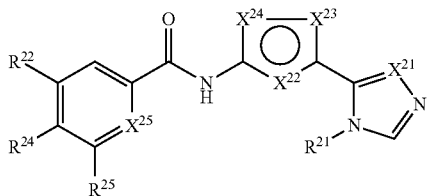

(II)

wherein:

R²¹ is alkyl, alkenyl, alkynyl, cycloalkyl, aryl, heteroaryl, or heterocyclyl, wherein the alkyl, alkenyl, alkynyl, cycloalkyl, aryl, heteroaryl, and heterocyclyl are optionally substituted with from one to four substituents independently selected from the group consisting of halo, hydroxyl, oxo, alkyl, cycloalkyl, heterocyclyl, aryl, aryloxy, NO₂, R²⁶, C(O)R²⁶, OC(O)R²⁶C(O)OR²⁶, C(O)N(R²⁶)(R²⁷), OC(O)N(R²⁶)(R²⁷), SR²⁶, S(═O)R²⁶, S(═O)₂R²⁶, S(═O)₂N(R²⁶)(R²⁷), S(═O)₂ OR²⁶, N(R²⁶)(R²⁷), N(R²⁶)C(O)R²⁷, N(R²⁶)C(O)OR²⁷, N(R²⁶)C(O)N(R²⁶)(R²⁷), N(R²⁶)S(═O)₂R²⁶, CN, and OR²⁶, wherein the alkyl, cycloalkyl, heterocyclyl, aryl, and aryloxy are optionally substituted with from one to three substituents independently selected from alkyl, cycloalkyl, alkoxy, hydroxyl, and halo;

R²⁶ and R²⁷ are independently selected from the group consisting of hydrogen, alkyl, cycloalkyl, heterocyclyl, aryl, and heteroaryl, wherein the alkyl, cycloalkyl, heterocyclyl, aryl, and heteroaryl are optionally substituted with from one to three substituents independently selected from halo, alkyl, monoalkylamino, dialkylamino, alkyl amide, aryl amide, heteroaryl amide, CN, lower alkoxy, CF₃, aryl, and heteroaryl; or R²⁶ and R²⁷ when taken together with the nitrogen to which they are attached form a heterocycle;

R²² is aryl, heteroaryl, or heterocyclyl, wherein the aryl, heteroaryl, and heterocyclyl are optionally substituted with from one to five substituents independently selected from alkyl, alkoxy, cycloalkyl, cycloalkylalkyl, aryl, arylalkyl, heteroaryl, heteroarylalkyl, heterocyclyl, heterocyclylalkyl, halo, oxo, NO₂, haloalkyl, haloalkoxy, CN, OR²⁶, OC(O)R²⁶, OC(O)N(R²⁶)(R²⁷), SR²⁶, N(R²⁶)(R²⁷), S(═O)R²⁶, S(═O)₂R²⁶, S(═O)₂N(R²⁶)(R²⁷), S(═O)₂OR²⁶, N(R²⁶)C(O)R²⁷, N(R²⁶)C(O)OR²⁷, N(R²⁶)C(O)N(R²⁶)(R²⁷), C(O)R²⁶, C(O)OR²⁶, C(O)N(R²⁶)(R²⁷), and N(R²⁶)S(═O)₂R²⁷, and wherein the alkyl, alkoxy, cycloalkyl, aryl, heteroaryl and heterocyclyl are optionally substituted with one or more substituents selected from halo, oxo, NO₂, alkyl, haloalkyl, haloalkoxy, N(R²⁶)(R²⁷), C(O)R²⁶, C(O)OR²⁶, C(O)N(R²⁶)(R²⁷), CN, OR²⁶, cycloalkyl, aryl, heteroaryl and heterocyclyl; with the proviso that the heteroaryl or heterocyclyl moiety includes at least one ring nitrogen atom;

R²⁴ and R²⁵ are independently hydrogen, halo, cyano, alkyl, alkoxy, or cycloalkyl, wherein the alkyl, alkoxy, and cycloalkyl are optionally substituted by halo or cycloalkyl;

X²¹ and X²⁵ are independently C(R²³) or N, wherein each R²³ is independently hydrogen, halo, alkyl, alkoxy or cycloalkyl, wherein the alkyl and cycloalkyl are optionally substituted with from one to five substituents independently selected from halo, oxo, CF₃, OCF₃, N(R²⁶)(R²⁷), C(O)R²⁶, C(O)OR²⁷, C(O)N(R²⁶)(R²⁷), CN, and OR²⁶; and X²², X²³ and X²⁴ are independently C(R²³), N, O, or S; with the proviso that at least one of X²², X²³, and X²⁴ is C(R²³); and only one of X²², X²³, and X²⁴ is O or S;

or a pharmaceutically acceptable salt, stereoisomer, or a mixture thereof.

3. A method of treating or preventing nonalcoholic steatohepatitis (NASH) in a patient in need thereof, comprising administering to the patient a therapeutically effective amount of an ASK1 inhibitor in combination with a therapeutically effective amount of a FXR agonist, wherein the ASK1 inhibitor is a compound of formula (III):

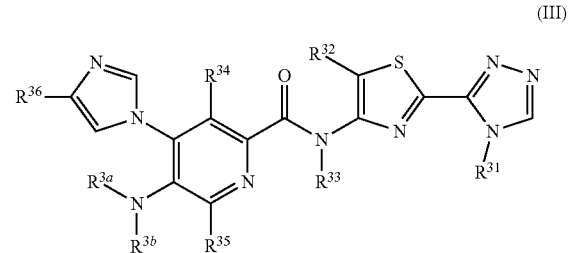

(III)

wherein:

R³¹ is $C_1$-$C_3$ alkyl or $C_3$-$C_6$ cycloalkyl, wherein the alkyl or cycloalkyl is optionally substituted with one to three halogen atoms;

R³² is hydrogen or $C_1$-$C_6$ alkyl wherein the alkyl is optionally substituted with halo;

R³³ is hydrogen or $C_1$-$C_3$ alkyl;

R³⁴ is hydrogen or $C_1$-$C_3$ alkyl;

$R^{35}$ is hydrogen, $C_1$-$C_3$ alkyl, $OR^{3a}$ or —$NHR^{3a}$;

$R^{36}$ is hydrogen, $C_1$-$C_3$ alkyl, $C_1$-$C_3$ haloalkyl, or $C_3$-$C_6$ cycloalkyl wherein the cycloalkyl is optionally substituted with $C_1$-$C_3$ alkyl, $C_1$-$C_3$ haloalkyl, or 1 or 2 halogen atoms;

$R^{3a}$ and $R^{3b}$ are independently hydrogen, $C_1$-$C_3$ alkyl or $R^{3a}$ and $R^{3b}$ combine with the nitrogen atom to which they are attached to form a four to six member heterocyclic ring optionally containing an oxygen or a nitrogen atom in the ring;

or a pharmaceutically acceptable salt, stereoisomer, or mixture thereof.

4. The method of claim 1, wherein the ASK1 inhibitor and the FXR agonist are administered together.

5. The method of claim 1, wherein the ASK1 inhibitor and the FXR agonist are administered separately.

6. A pharmaceutical composition comprising a therapeutically effective amount of an ASK1 inhibitor and a therapeutically effective amount of a FXR agonist, wherein the ASK1 inhibitor is a compound of formula (I):

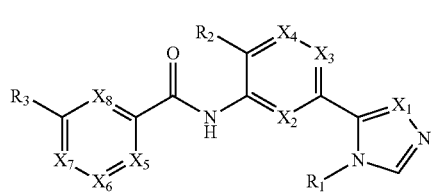

wherein:

$R^1$ is alkyl, alkenyl, alkynyl, cycloalkyl, aryl, heteroaryl, or heterocyclyl, wherein the alkyl, alkenyl, alkynyl, cycloalkyl, aryl, heteroaryl, and heterocyclyl are optionally substituted with from one to three substituents independently selected from halo, oxo, alkyl, cycloalkyl, heterocyclyl, aryl, aryloxy, —$NO_2$, $R^6$, —C(O)—$R^6$, —OC(O)—$R^6$ —C(O)—O—$R^6$, C(O)—N($R^6$)($R^7$), —OC(O)—N($R^6$)($R^7$), —S—$R^6$, —S(=O)—$R^6$, —S(=O)$_2R^6$, —S(=O)$_2$—N($R^6$)($R^7$), —S(=O)$_2$—O—$R^6$, —N($R^6$)($R^7$), —N($R^6$)—C(O)—$R^7$, —N($R^6$)—C(O)—O—$R^7$, —N($R^6$)—C(O)—N($R^6$)($R^7$), —N($R^6$)—S(=O)$_2$—$R^6$, —CN, and —O—$R^6$, and wherein the alkyl, cycloalkyl, heterocyclyl, aryl, and aryloxy are optionally substituted by from one to three substituents independently selected from alkyl, cycloalkyl, alkoxy, hydroxyl, and halo; wherein $R^6$ and $R^7$ are independently selected from the group consisting of hydrogen, $C_1$-$C_{15}$ alkyl, cycloalkyl, heterocyclyl, aryl, and heteroaryl, all of which are optionally substituted with from one to three substituents independently selected from halo, alkyl, monoalkylamino, dialkylamino, alkyl amide, aryl amide, heteroaryl amide, —CN, lower alkoxy, —$CF_3$, aryl, and heteroaryl; or $R^6$ and $R^7$ when taken together with the nitrogen to which they are attached form a heterocycle;

$R^2$ is hydrogen, halo, cyano, alkoxy, or alkyl optionally substituted by halo;

$R^3$ is aryl, heteroaryl, or heterocyclyl, wherein the aryl, heteroaryl, and heterocyclyl are optionally substituted with from one to five substituents independently selected from alkyl, alkoxy, cycloalkyl, cycloalkylalkyl, aryl, arylalkyl, heteroaryl, heteroarylalkyl, heterocyclyl, heterocyclylalkyl, halo, oxo —$NO_2$, haloalkyl, haloalkoxy, —CN, —O—$R^6$, —O—C(O)—$R^6$, —O—C(O)—N($R^6$)($R^7$), —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—$R^6$, —C(O)—N($R^6$)($R^7$), and —N($R^6$)—S(=O)$_2$—$R^7$, wherein the alkyl, alkoxy, cycloalkyl, aryl, heteroaryl or heterocyclyl is optionally substituted with from one to five substituents independently selected from halo, oxo, —$NO_2$, alkyl, haloalkyl, haloalkoxy, —N($R^6$)($R^7$), —C(O)—$R^6$, —C(O)—O—$R^6$, —C(O)—N($R^6$)($R^7$), —CN, —O—$R^6$, cycloalkyl, aryl, heteroaryl and heterocyclyl; with the proviso that the heteroaryl or heterocyclyl moiety of $R^3$ includes at least one ring nitrogen atom;

$X^1$, $X^2$, $X^3$, $X^4$, $X^5$, $X^6$, $X^7$ and $X^8$ are independently $C(R^4)$ or N, in which each $R^4$ is independently hydrogen, alkyl, alkoxy, cycloalkyl, aryl, heteroaryl, heterocyclyl, halo, —$NO_2$ haloalkyl, haloalkoxy, —CN, —O—$R^6$, —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—O—$R^6$, —C(O)—N($R^6$)($R^7$), or —N($R^6$)—S(=O)$_2$—$R^7$, wherein the alkyl, cycloalkyl, aryl, heteroaryl, and heterocyclyl is further optionally substituted with from one to five substituents independently selected from halo, oxo, —$NO_2$—$CF_3$—O—$CF_3$, —N($R^6$)($R^7$), —C(O)—$R^6$, —C(O)—O—$R^7$, —C(O)—N($R^6$)($R^7$), —CN, —O—$R^6$; or $X^5$ and $X^6$ or $X^6$ and $X^7$ are joined to provide optionally substituted fused aryl or optionally substituted fused heteroaryl; and with the proviso that at least one of $X^2$, $X^3$, and $X^4$ is $C(R^4)$; at least two of $X^5$, $X^6$, $X^7$, and $X^8$ are $C(R^4)$; and at least one of $X^2$, $X^3$, $X^4$, $X^5$, $X^6$, $X^7$ and $X^8$ is N;

or a pharmaceutically acceptable salt, stereoisomer, or a mixture thereof.

7. The pharmaceutical composition of claim 6, further comprising a pharmaceutically acceptable carrier.

8. The method of claim 1, wherein the ASK1 inhibitor is selected from the group consisting of:

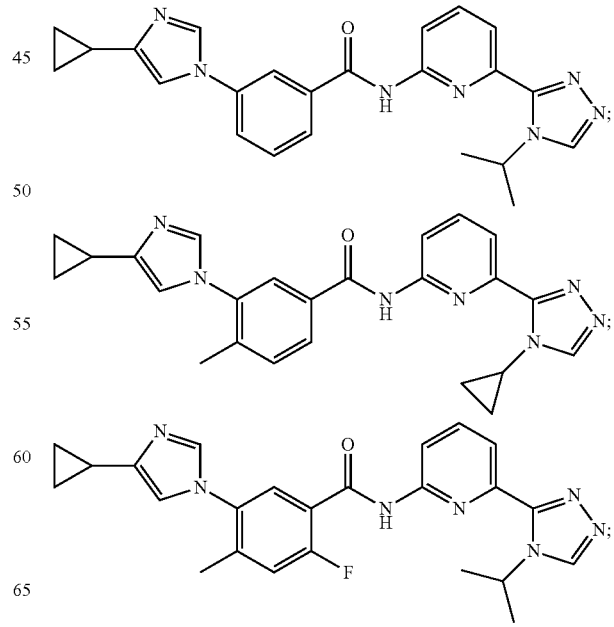

-continued

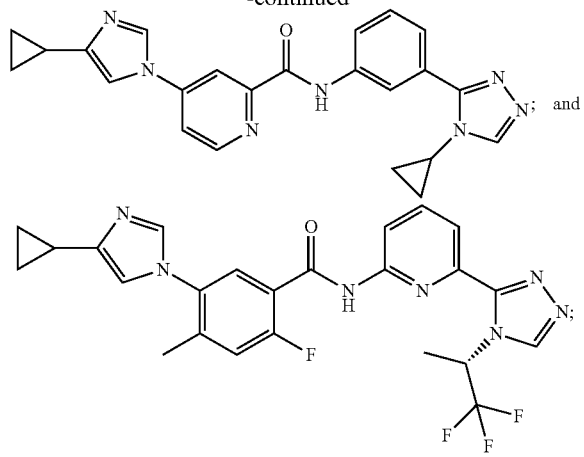

or a pharmaceutically acceptable salt thereof.

9. The method of claim 1, wherein the ASK1 inhibitor is a compound having the following structure:

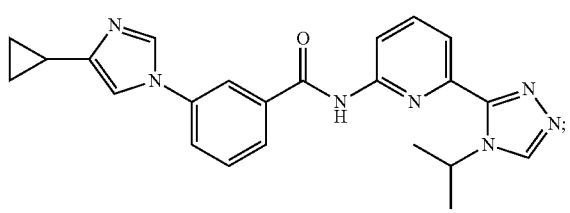 [SMILES: CC(C)n1cnnc1-c1cccc(NC(=O)c2cccc(-n3cnc(C4CC4)c3)c2)n1]

or a pharmaceutically acceptable salt thereof.

10. The pharmaceutical composition of claim 6, wherein the ASK1 inhibitor is a compound having the following structure:

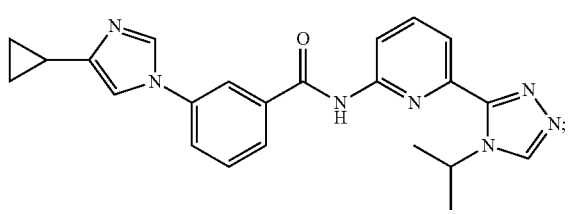

or a pharmaceutically acceptable salt thereof.

11. The method of claim 1, wherein the ASK1 inhibitor is a compound having the following structure:

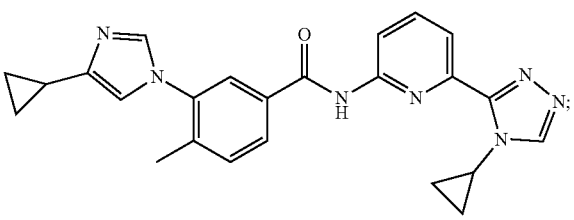 [SMILES: Cc1ccc(C(=O)Nc2cccc(-c3nncn3C3CC3)n2)cc1-n1cnc(C2CC2)c1]

or a pharmaceutically acceptable salt thereof.

12. The pharmaceutical composition of claim 6, wherein the ASK1 inhibitor is a compound having the following structure:

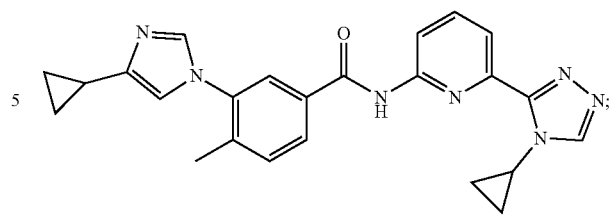

or a pharmaceutically acceptable salt thereof.

13. The method of claim 1, wherein the ASK1 inhibitor is a compound having the following structure:

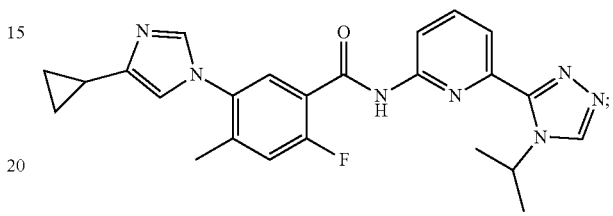

or a pharmaceutically acceptable salt thereof.

14. The pharmaceutical composition of claim 6, wherein the ASK1 inhibitor is a compound having the following structure:

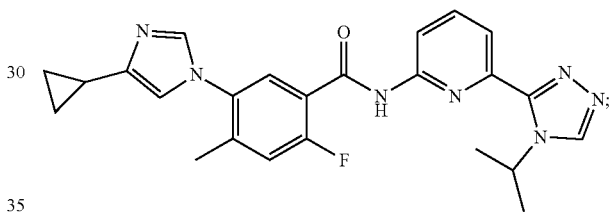

or a pharmaceutically acceptable salt thereof.

15. The method of claim 1, wherein the ASK1 inhibitor is a compound having the following structure:

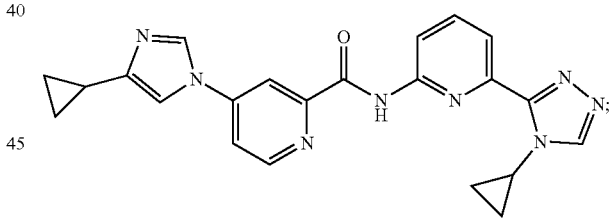

or a pharmaceutically acceptable salt thereof.

16. The pharmaceutical composition of claim 6, wherein the ASK1 inhibitor is a compound having the following structure:

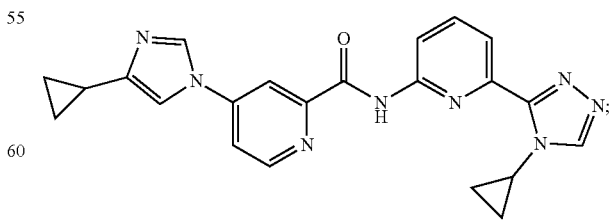

or a pharmaceutically acceptable salt thereof.

17. The method of claim 1, where in the ASK1 inhibitor is a compound having the following structure:

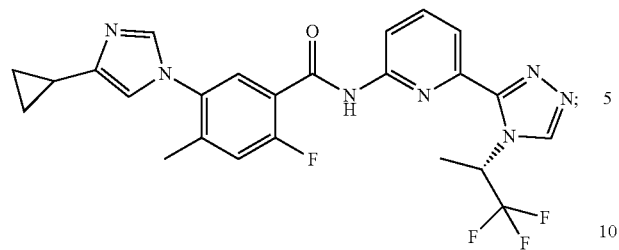
or a pharmaceutically acceptable salt thereof.
18. The pharmaceutical composition of claim 6, wherein the ASK1 inhibitor is a compound having the following structure:
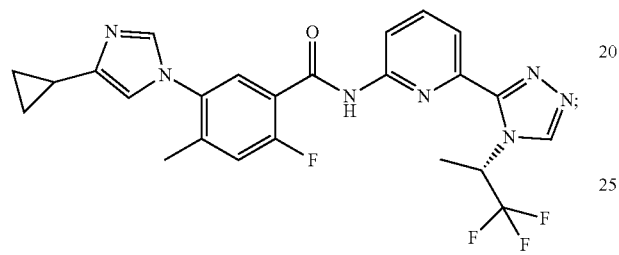
or a pharmaceutically acceptable salt thereof.
* * * * *